(12) United States Patent
Lyga et al.

(10) Patent No.: US 8,017,635 B2
(45) Date of Patent: Sep. 13, 2011

(54) PHENYLALKYL SUBSTITUTED HETEROARYL DERIVATIVES

(75) Inventors: John W. Lyga, Basking Ridge, NJ (US); Frank Zawacki, Yardley, PA (US); Larry Y. Zhang, Kendall Park, NJ (US)

(73) Assignee: FMC Corporation, Philadelphia, PA (US)

( * ) Notice: Subject to any disclaimer, the term of this patent is extended or adjusted under 35 U.S.C. 154(b) by 284 days.

(21) Appl. No.: 11/915,974

(22) PCT Filed: May 24, 2006

(86) PCT No.: PCT/US2006/020049
§ 371 (c)(1),
(2), (4) Date: Oct. 20, 2009

(87) PCT Pub. No.: WO2006/130403
PCT Pub. Date: Dec. 7, 2006

(65) Prior Publication Data
US 2010/0152045 A1   Jun. 17, 2010

Related U.S. Application Data
(60) Provisional application No. 60/686,874, filed on Jun. 2, 2005.

(51) Int. Cl.
| | | |
|---|---|---|
| *A61K 31/41* | (2006.01) | |
| *A61K 31/415* | (2006.01) | |
| *C07D 207/00* | (2006.01) | |
| *C07D 233/00* | (2006.01) | |
| *C07D 249/00* | (2006.01) | |

(52) U.S. Cl. ........ 514/359; 514/383; 514/403; 514/408; 548/250; 548/255; 548/262.2; 548/300.1; 548/356.1; 548/400

(58) Field of Classification Search .................. 548/250, 548/255, 262, 2, 300.1, 356.1, 400
See application file for complete search history.

(56) References Cited

U.S. PATENT DOCUMENTS

| | | | |
|---|---|---|---|
| 4,387,100 A | 6/1983 | Machin | |
| 4,577,030 A | 3/1986 | Machin | |
| 4,663,462 A | 5/1987 | Machin | |
| 5,922,880 A * | 7/1999 | Sakamoto et al. | 546/296 |
| 6,071,861 A * | 6/2000 | Sakamoto et al. | 504/288 |
| 6,268,313 B1 * | 7/2001 | Sakamoto et al. | 504/266 |
| 6,987,194 B2 | 1/2006 | Theodoridis et al. | |
| 7,208,450 B2 * | 4/2007 | Theodoridis et al. | 504/270 |
| 2006/0094776 A1 | 5/2006 | Theodoridis et al. | |
| 2006/0247283 A1 | 11/2006 | Theodoridis et al. | |
| 2006/0270726 A1 | 11/2006 | Theodoridis et al. | |

FOREIGN PATENT DOCUMENTS
WO    WO 03/074498 A1    9/2003

OTHER PUBLICATIONS

Machin, P.J., et al., "$\beta_1$-Selective Adrenoceptor Antagonists. 3. 4-Azolyl-Linked Phenoxypropanolamines," *J. Med. Chem.* 27:503-509, American Chemical Society (1984).
International Search Report for International Application No. PCT/US06/20049, United States Patent and Trademark Office, Alexandria, VA, mailed on Oct. 4, 2006.
International Preliminary Report on Patentability for International Application No. PCT/US06/20049, The International Bureau of WIPO, Geneva, Switzerland, issued on Dec. 6, 2007.
Co-pending U.S. Appl. No. 11/569,188, inventors Barron, E.J., et al., filed May 18, 2005 (Not Published).

* cited by examiner

*Primary Examiner* — Susannah Chung

(57) ABSTRACT

Certain novel phenylalkyl substituted azole derivatives have unexpected insecticidal activity. These compounds are represented by formula I: where A, B, D, E, G, a, b, c, d, and R through $R^{11}$, inclusively, are folly described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

(I)

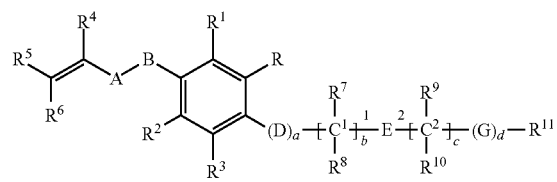

7 Claims, No Drawings

PHENYLALKYL SUBSTITUTED HETEROARYL DERIVATIVES

This application is a U.S. National Stage of International Application No. PCT/US2006/020049, filed May 24, 2006, which claims the benefit of U.S. Application No. 60/686,874, filed Jun. 2, 2005. The entirety of each of these applications is incorporated by reference herein.

FIELD OF THE INVENTION

The present invention relates to novel compounds and their use in controlling insects and acarids. In particular, it pertains to phenylalkyl substituted heteroaryl derivatives and agriculturally acceptable salts thereof, compositions containing them and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs.

Such damage may result in the loss of millions of dollars of value associated with a given crop, turf or structures. Insecticides and acaricides are useful for controlling insects and acarids which may otherwise cause significant damage to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of patents and publications disclose a variety of dihalopropene compounds that are reported to be insecticidally and acaricidally active. For example, U.S. Pat. No. 5,922,880 discloses certain dihalopropene compounds for use as insecticides and acaricides of the general formula:

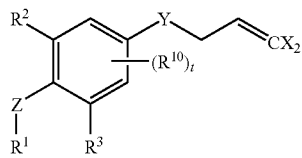

where $R^1$, $R^2$, $R^3$, $R^{10}$, X, Y, Z and t are fully described therein.

PCT publication WO 2003074498 discloses a class of cyclic diamine compounds of the following formula useful as pesticides:

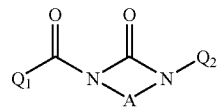

where
A, Q1 and Q2 are fully described therein.

There is no disclosure or suggestion in any of the above-referenced patents of the structures and pesticidal activity of the compounds of the present invention.

SUMMARY OF THE INVENTION

In accordance with the present invention, it has now been found that certain novel phenylalkyl substituted heteroaryl derivatives are surprisingly active in the control of insects and acarids when used in the insecticidal and acaricidal compositions and methods of this invention. The novel derivatives are represented by the following general formula I:

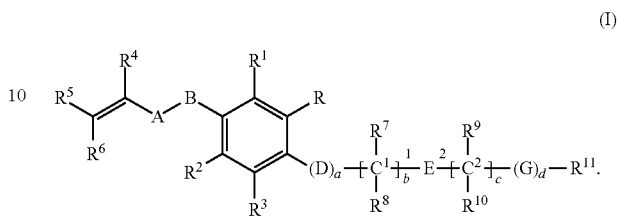

where

R and $R^3$ are independently selected from hydrogen, halogen, hydroxy, $(C_1-C_6)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$alkylsulfonyl, halo$(C_1-C_3)$alkylsulfonyl, cyano, nitro, amino; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=K)-L, and —C($R^{17}$)-M-$R^{18}$, wherein the optional substituent is selected from $(C_1-C_4)$alkyl, halogen, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where

K is selected from O, S, $NR^{19}$, and $NOR^{19}$, where $R^{19}$ is hydrogen, $(C_1-C_4)$alkyl, halo$(C_1-C_4)$alkyl, aryl and aryl$(C_1-C_4)$alkyl;

L is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;

M is selected from O, S, and $NR^{19}$, where $R^{19}$ is as previously described;

$R^{17}$ and $R^{18}$ are independently selected from hydrogen, $(C_1-C_4)$alkyl and halo$(C_1-C_4)$alkyl, or $R^{17}$ and $R^{18}$ are taken together with -Q(CHR$^{19}$)$_e$—, where e is an integer of 2 to 4; Q is selected from O, S, and $NR^{19}$, where $R^{19}$ is as previously described;

$R^1$ and $R^2$ are independently selected from hydrogen, halogen and $(C_1-C_3)$alkyl;

A is selected from O, S, *OCH$_2$ and (CH$_2$)$_f$ where the asterisk denotes attachment to B, and f is an integer selected from 1, 2 and 3;

B is selected from CH$_2$, O, S and NR$^{20}$ where R$^{20}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo$(C_2-C_4)$alkenyl$(C_1-C_3)$alkyl, di$(C_1-C_3)$alkylphosphonate, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl; provided that A and B are not simultaneously O or S;

R[4] is hydrogen;

R[5] and R[6] are independently selected from halogen;

a is an integer selected from 0 or 1;

and when a is 1,

D is O, $CH_2$, $OCH_2$, $CH_2O$, OCH=CH, C(=O), $S(O)_g$, CH=CH, OC(=O), OC(=O)NH, NHC(=O), $NHSO_2$, N=CH, and $NR^{20}$, or $N(oxide)R^{20}$ where $R^{20}$ is as previously described, and g is an integer selected from 0, 1 or 2;

b is an integer selected from 0, 1, 2, 3, or 4;

and when b is 1 or more,

R[7] and R[8] are independently selected from hydrogen, halogen, $(C_1-C_4)$alkyl, cyclo$(C_3-C_6)$alkyl, halo$(C_1-C_4)$alkyl, or aryl;

E is selected from

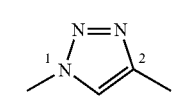 (E1)

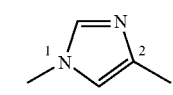 (E2)

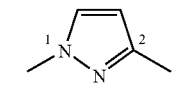 (E3)

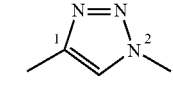 (E4)

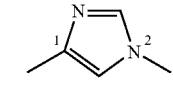 (E5)

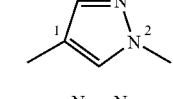 (E6)

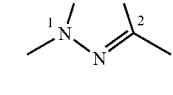 (E7)

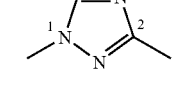 (E8)

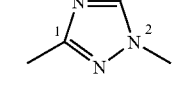 (E9)

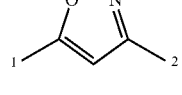 (E10)

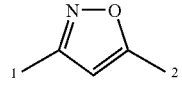 (E11)

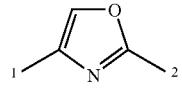 (E12)

-continued

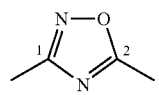 (E13)

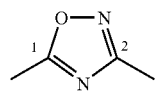 (E14)

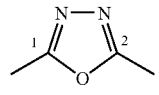 (E15)

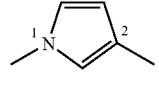 (E16)

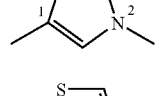 (E17)

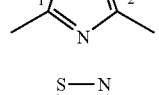 (E18)

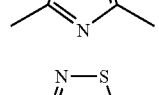 (E19)

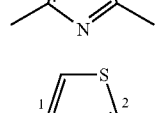 (E20)

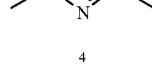 (E21)

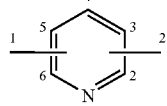 (E22)

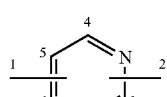 (E23)

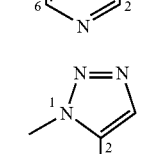 (E24)

(E25)

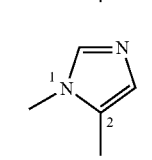 (E26)

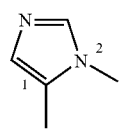 (E27)

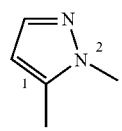 (E28)

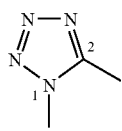 (E29)

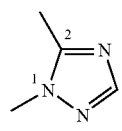 (E30)

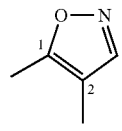 (E31)

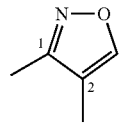 (E32)

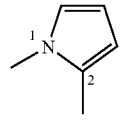 (E33)

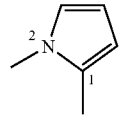 (E34)

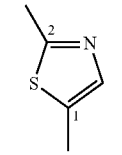 (E35)

where 1 and 2 indicate the bond of attachment in formula I,
c is an integer selected from 0, 1, 2, 3 or 4;
and when c is 1 or more,
$R^9$ and $R^{10}$ are independently selected from hydrogen, $(C_1-C_4)$alkyl, halo$(C_1-C_4)$alkyl or $(C_1-C_4)$alkoxy, and aryl;
d is an integer selected from 0 or 1; and,
when d is 1,
G is selected from O, CH=CH, S(O)$_g$, HC=N, C(=O), OC(=O), C(=O)O, C(=O)NH, NR$^{20}$, N(oxide)R$^{20}$ and NR$^{20}$C(=O) where g and R$^{20}$ are as previously described;
$R^{11}$ is selected from $(C_1-C_6)$alkyl, tri$(C_1-C_6)$alkylsilyl,

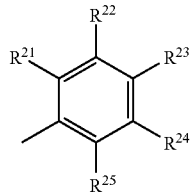 (R$^{11}$-1)

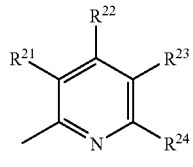 (R$^{11}$-2)

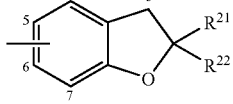 (R$^{11}$-3)

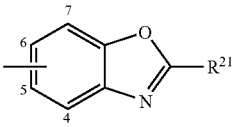 (R$^{11}$-4)

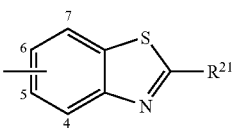 (R$^{11}$-5)

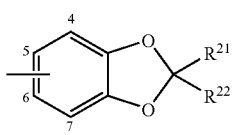 (R$^{11}$-6)

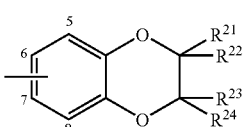 (R$^{11}$-7)

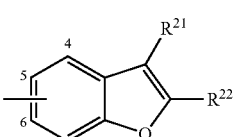 (R$^{11}$-8)

wherein $R^{21}$ through $R^{25}$ are independently selected from hydrogen, halogen, $(C_1-C_6)$alkyl, $(C_2-C_4)$alkenyl, $(C_2-C_4)$alkynyl, halo$(C_1-C_6)$alkyl, hydroxy$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy$(C_1-C_6)$alkyl, $(C_2-C_4)$alkenyloxy, $(C_2-C_4)$alkynyloxy, halo$(C_1-C_6)$alkoxy, halo$(C_2-C_4)$alkenyloxy, halo$(C_2-C_4)$alkynyloxy, $(C_1-C_6)$alkylthio, pentahalothio, $(C_1-C_6)$alkylsulfinyl, $(C_1-C_6)$alkylsulfonyl, halo$(C_1-C_6)$alkylthio, halo$(C_1-C_6)$alkylsulfinyl, halo$(C_1-C_6)$alkylsulfonyl, cyano, nitro; NR$^c$R$^d$, where R$^c$ and R$^d$ are independently selected from hydrogen, $(C_1-C_6)$alkyl, halo$(C_1-C_6)$alkyl, $(C_1-C_6)$alkoxy, $(C_1-C_6)$alkylcarbonyl, and $(C_1-C_6)$alkoxycarbonyl, or R$^c$ and R$^d$ are taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$alkylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy;

and agriculturally-acceptable salts thereof.

The present invention also includes compositions containing an insecticidally effective amount of at least one compound of formula I, and optionally, an effective amount of at least one additional compound, with at least one insecticidally compatible carrier.

The present invention also includes methods of controlling insects, in an area where control is desired, which comprise applying an insecticidally effective amount of the above composition to the locus of crops, or other areas where insects are present or are expected to be present.

The present invention also includes novel intermediates finding utility in the syntheses of compounds of formula I.

DETAILED DESCRIPTION OF THE INVENTION

The present invention relates to certain new and useful insecticidal and acaricidal compounds, namely phenylalkyl substituted heteroaryl derivatives (hereinafter termed "compounds of formula I") as depicted in general formula I:

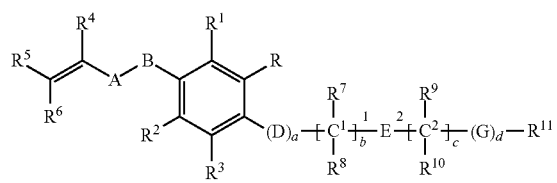

I where

R and $R^3$ are independently selected from hydrogen, halogen, hydroxy, $(C_1-C_6)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$allylsulfonyl, halo$(C_1-C_3)$alkylsulfonyl, cyano, nitro, amino; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=K)-L, and —C($R^{17}$)-M-$R^{18}$, wherein the optional substituent is selected from $(C_1-C_4)$alkyl, halogen, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where

K is selected from O, S, $NR^{19}$, and $NOR^{19}$, where $R^{19}$ is hydrogen, $(C_1-C_4)$alkyl, halo$(C_1-C_4)$alkyl, aryl and aryl$(C_1-C_4)$alkyl;

L is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;

M is selected from O, S, and $NR^{19}$, where $R^{19}$ is as previously described;

$R^{17}$ and $R^{18}$ are independently selected from hydrogen, $(C_1-C_4)$alkyl and halo$(C_1-C_4)$alkyl, or $R^{17}$ and $R^{18}$ are taken together with -Q(CHR$^{19}$)$_e$—, where e is an integer of 2 to 4; Q is selected from O, S, and $NR^{19}$, where $R^{19}$ is as previously described;

$R^1$ and $R^2$ are independently selected from hydrogen, halogen and $(C_1-C_3)$alkyl;

A is selected from O, S, *OCH$_2$ and (CH$_2$)$_f$ where the asterisk denotes attachment to B, and f is an integer selected from 1, 2 and 3;

B is selected from CH$_2$, O, S and $NR^{20}$ where $R^{20}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo$(C_2-C_4)$alkenyl$(C_1-C_3)$alkyl, di$(C_1-C_3)$alkylphosphonate, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl; provided that A and B are not simultaneously O or S;

$R^4$ is hydrogen;

$R^5$ and $R^6$ are independently selected from halogen;

a is an integer selected from 0 or 1;

and when a is 1,

D is O, CH$_2$, OCH$_2$, CH$_2$O, OCH=CH, C(=O), S(O)$_g$, CH=CH, OC(=O), OC(O)NH, NHC(=O), NHSO$_2$, N=CH, and $NR^{20}$, or N(oxide)$R^{20}$ where $R^{20}$ is as previously described, and g is an integer selected from 0, 1 or 2;

b is an integer selected from 0, 1, 2, 3, or 4;

and when b is 1 or more, $R^7$ and $R^8$ are independently selected from hydrogen, halogen, $(C_1-C_4)$alkyl, cyclo$(C_3-C_6)$alkyl, halo$(C_1-C_4)$alkyl, or aryl;

E is selected from

 (E1)

 (E2)

 (E3)

 (E4)

 (E5)

 (E6)

 (E7)

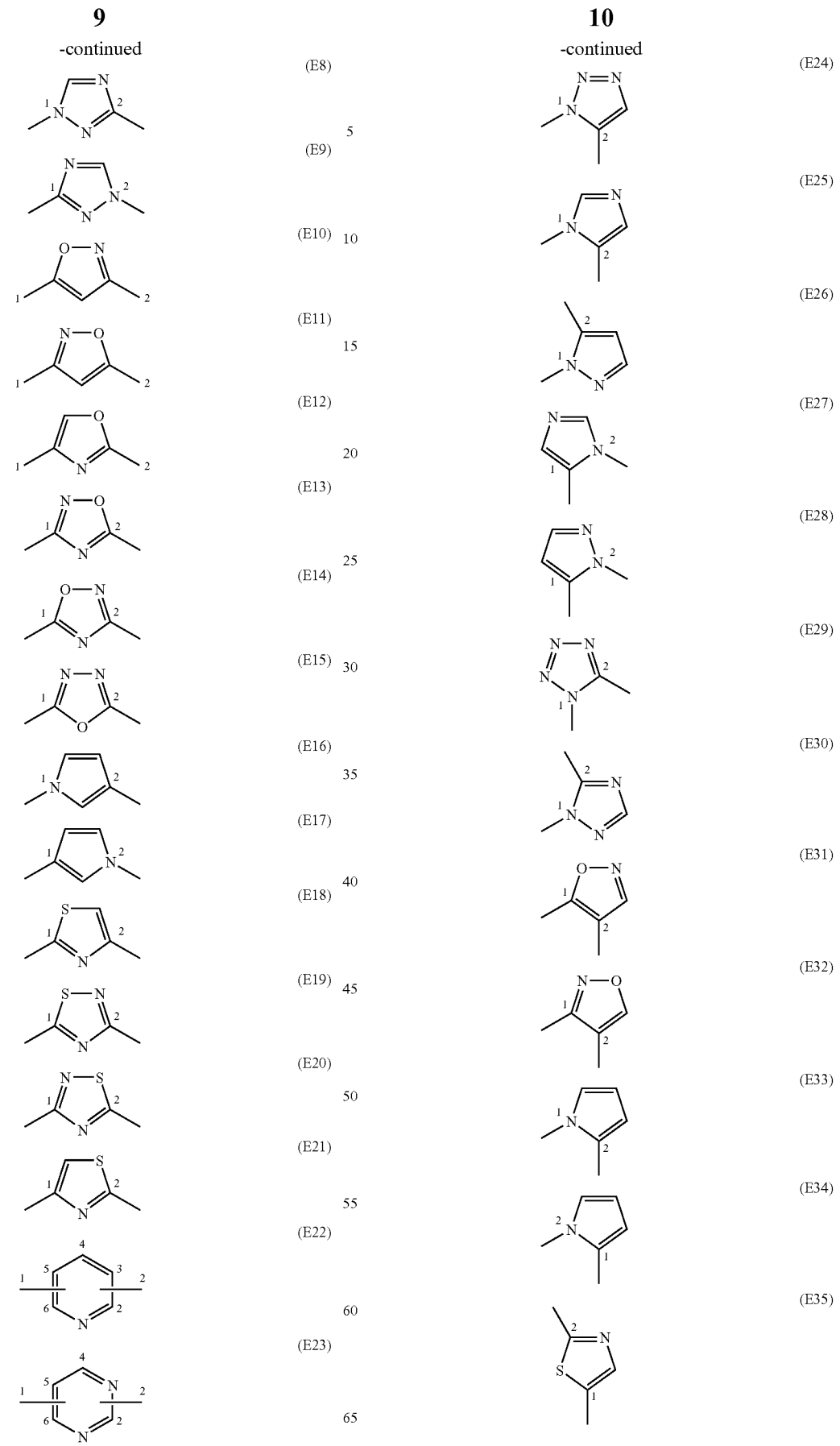

where 1 and 2 indicate the bond of attachment in formula I,
c is an integer selected from 0, 1, 2, 3 or 4;
and when c is 1 or more,
$R^9$ and $R^{10}$ are independently selected from hydrogen, $(C_1-C_4)$alkyl, halo$(C_1-C_4)$alkyl or $(C_1-C_4)$alkoxy, or aryl;
d is an integer selected from 0 or 1; and,
when d is 1,
G is selected from O, CH=CH, S(O)$_g$, HC=N, C(=O), OC(=O), C(=O)O, C(=O)NH, NR$^{20}$, N(oxide)R$^{20}$ and NR$^{20}$C(=O) where g and R$^{20}$ are as previously described;
$R^{11}$ is selected from $(C_1-C_6)$alkyl, tri$(C_1-C_6)$alkylsilyl,

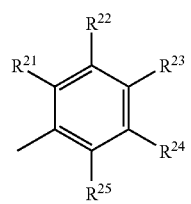
(R$^{11}$-1)

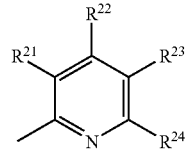
(R$^{11}$-2)

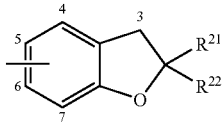
(R$^{11}$-3)

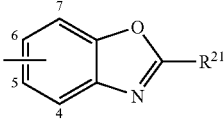
(R$^{11}$-4)

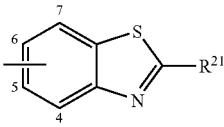
(R$^{11}$-5)

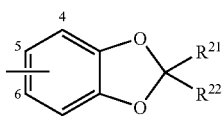
(R$^{11}$-6)

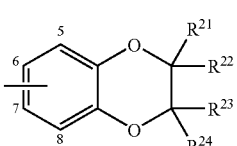
(R$^{11}$-7)

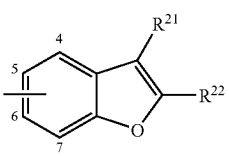
(R$^{11}$-8)

wherein $R^{21}$ through $R^{25}$ are independently selected from hydrogen, halogen, $(C_1-C_6)$alkyl, $(C_2-C_4)$alkenyl, $(C_2-C_4)$alkynyl, halo$(C_1-C_6)$alkyl, hydroxy$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy$(C_1-C_6)$alkyl, $(C_2-C_4)$alkenyloxy, $(C_2-C_4)$alkynyloxy, halo$(C_1-C_6)$alkoxy, halo$(C_2-C_4)$alkenyloxy, halo$(C_2-C_4)$alkynyloxy, $(C_1-C_6)$alkylthio, pentahalothio, $(C_1-C_6)$alkylsulfinyl, $(C_1-C_6)$allylsulfonyl, halo$(C_1-C_6)$alkylthio, halo$(C_1-C_6)$alkylsulfinyl, halo$(C_1-C_6)$alkylsulfonyl, cyano, nitro; NR$^c$R$^d$, where R$^c$ and R$^d$ are independently selected from hydrogen, $(C_1-C_6)$alkyl, halo$(C_1-C_6)$alkyl, $(C_1-C_6)$alkoxy, $(C_1-C_6)$alkylcarbonyl, and $(C_1-C_6)$alkoxycarbonyl, or R$^c$ and R$^d$ are taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$allylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy;
and
agriculturally-acceptable salts thereof.

Preferred phenylalkyl substituted azole derivatives from the group set forth above are those where:
R and $R^3$ are independently selected from halogen and $(C_1-C_3)$alkyl;
$R^1$, $R^2$ and $R^4$ are hydrogen;
$R^5$ and $R^6$ are halogen;
A is (CH$_2$)$_f$ where f is 1;
B is O;
a is an integer selected from 0 or 1, and when a is 1, D is selected from O, CH$_2$ and OCH$_2$;
b is an integer selected from 0, 1, 2, 3 or 4, and when b is 1 or more, $R^7$ and $R^8$ are each hydrogen;
E is formula (E1), formula (E4), formula (71), or formula (E8);
c is an integer selected from 0, 1, 2, 3 and 4, and when c is 1 or more, $R^9$ and $R^{10}$ are each hydrogen;
d is 0 or 1; and when d is 1, G is selected from O or S; and
$R^{11}$ is selected from formula (R$^{11}$-1), formula (R$^{11}$-2), formula (R$^{11}$-3), or formula (R$^{11}$-4).

More preferred phenylalkyl substituted heteroaryl derivatives of the group set forth above are those where:
R and $R^3$ are each chlorine;
a is 1 and D is O;
b is an integer selected from 2, 3 or 4;
E is formula (E1) or formula (E7);
c is an integer selected from 0 or 1;
d is 0; and
$R^{11}$ is (R$^{11}$-1) or (R$^{11}$-2).

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention comprise causing an insecticidally effective amount of a compound of formula I to be administered to insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which are referred to as pro-insecticides.

Another aspect of the present invention relates to compositions containing an insecticidally effective amount of at least one compound of formula I.

Another aspect of the present invention relates to compositions containing an insecticidally effective amount of at least one compound of formula I, and an effective amount of at least one additional compound.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The terms "haloalkyl" and "haloalkoxy" used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms, wherein one or more hydrogen atoms have been replaced with halogen atoms, for example, trifluoromethyl or 2,2,2-trifluoroethoxy. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having six to ten carbon atoms, for example, phenyl, indanyl, indenyl, naphthyl or 5,6,7,8-tetrahydronaphthyl. The term "heteroaryl" refers to an aromatic ring structure, including fused rings, in which at least one of the atoms is other than carbon, for example, without limitation, sulfur, oxygen, or nitrogen. Heteroaryl rings include, without limitation, for example, oxazolyl, thiazolyl, imidazolyl, pyrazolyl, triazolyl or thiadiazolyl. The term "DMP" refers to N,N-dimethylformamide. The term "THF" refers to tetrahydrofuran. The term "TEA" refers to triethyl amine. The term "DIEA" refers to N,N-diisopropylethylamine. The term "HBTU" refers to O-benzotriazol-1-yl-N,N,N',N'-tetramethyluronium hexafluorophosphate. The term "HOBT" refers to 1-hydroxybenzotriazole hydrate. The term "TFA" refers to trifluoroacetic acid. The term "halogen" or "halo" refers to fluorine, bromine, iodine, or chlorine. The term "ambient temperature", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one additional compound, or with at least one compatible carrier, which causes the destruction or the inhibition of action of insects or acarids. The term "independently selected from" as set forth above and in the claims section of the present specification refers to the possibility that moieties, for example $R^5$ and $R^6$, may be the same or they may be different within the group that the selection is made.

The phenylalkyl substituted heteroaryl derivatives of formula I can be synthesized by methods that are individually known to one skilled in the art from available intermediate compounds.

Scheme 1 below illustrates a general procedure for synthesizing phenylalkyl substituted heteroaryl derivatives of formula I, inter alia, where, for example, $R^1$, $R^2$, $R^4$, $R^7$, $R^8$ are hydrogen; R, $R^3$, $R^5$ and $R^6$ are chlorine; A is $(CH_2)_f$ where f is 1; B is O, a is 1, and D is O; b is 2; E is (E1); c and d are 0; $R^{11}$ is 4-chlorophenyl:

Scheme 1:

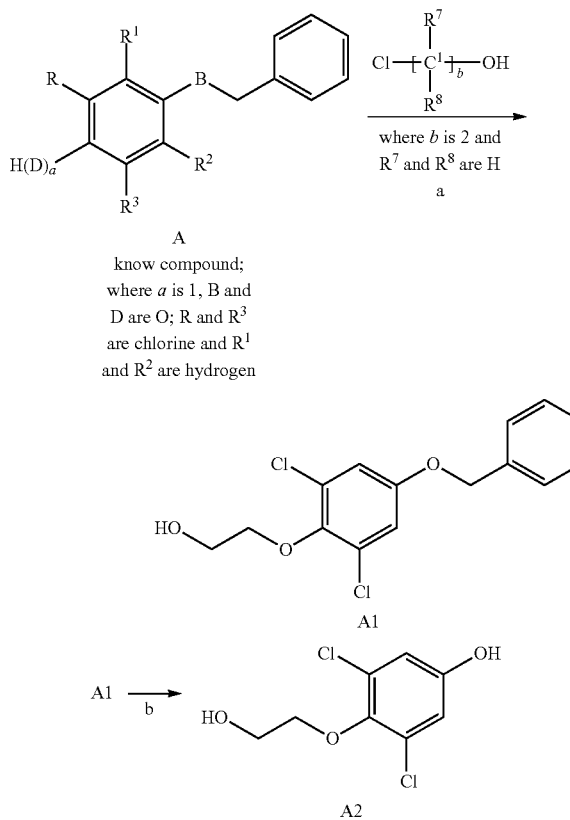

-continued

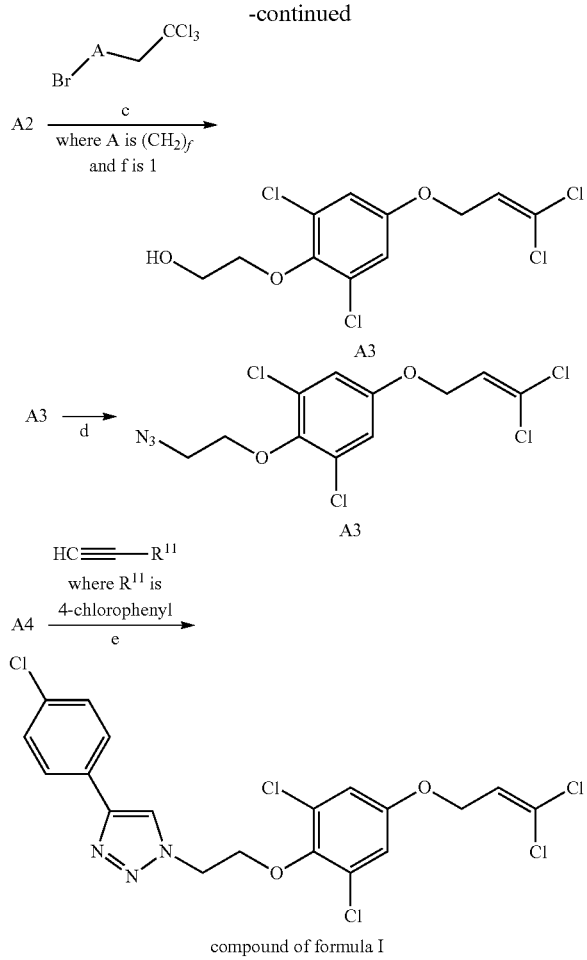

compound of formula I a) K$_2$CO$_3$/DMF/80° C. b) H$_2$/10% Pd on carbon/EtOH c) K$_2$CO$_3$/DMF/95° C. d) (1)Methanesulfonyl chloride/TEA/CH$_2$Cl$_2$ (2) DMSO/NaN$_3$ e) t-butanol:water (1:1)/sodium ascorbate/copper (II) sulfate pentahydrate As depicted in scheme 1, the known compound 2,6-dichloro-4-phenylmethoxyphenol was reacted under basic conditions with, for example a haloalkyl alcohol such as 2-chloroethanol, affording the corresponding alcohol (A1), for example, 2-(2,6-dichloro-4-(phenylmethoxy)phenoxy) ethan-1-ol. Intermediate (A1) was treated it with hydrogen gas under catalytic hydrogenation conditions, providing intermediate (A2). Intermediate (A2) was treated with, for example 3-bromo-1,1,1-trichloropropane, under basic conditions, affording the corresponding intermediate (A3). Intermediate (A3) was reacted with methanesulfonyl chloride under basic conditions to form a mesylate intermediate which was treated with sodium azide in an appropriate solvent to afford the corresponding azidoethanol intermediate (A4), for example, 4-(3,3-dichloroprop-2-enyloxy)-2,6-dichloro-1-(2-azidoethoxy)benzene. The azidoethanol intermediate (A4) was reacted with an appropriately substituted ethynylbenzene in the presence of sodium ascorbate and a catalytic amount of copper (II) sulfate pentahydrate, providing compounds of formula I, such as, 5-(3,3-dichloroprop-2-enyloxy)-1,3-dichloro-2-(2-(4-(4-chlorophenyl)1,2,3-triazolyl)ethoxy) benzene. This process is described in detail in Example 1 set forth below.

Scheme 2 below illustrates a general procedure for synthesizing phenylalkyl substituted heteroaryl derivatives of formula I, inter alia, where, for example, R$^1$, R$^2$, R$^4$R$^7$, R$^8$ are hydrogen; R, R$^3$, R$^5$ and R$^6$ are chlorine; A is (CH$_2$)$_f$ where f is 1; B is O, a is 1, and D is O; b is 2; E is (E7); c and d are 0; R$^{11}$ is 3-trifluoromethylphenyl:

Scheme 2:

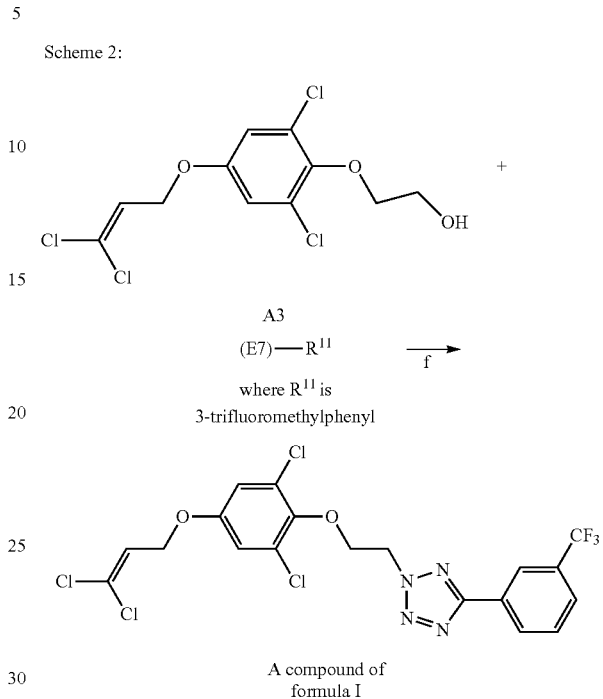

f) PPh3, diisopropyl azodicarboxylate, THF

As depicted in scheme 2, the reaction of intermediate (A3) with an appropriately substituted tetrazole, for example 5-(3-trifluoromethylphenyl)-2H-1,2,3,4-tetraazole, in the presence of triphenylphosphine and diisopropyl azodicarboxylate in an appropriate solvent to provide compounds of formula I where E is formula (E7), for example, 5-(3,3-dichloroprop-2-enyloxy)-1,3-dichloro-2(-2-(5-(3-trifluoromethylphenyl) (1,2,3,4-tetrazol-2-yl))ethoxy)benzene. This process is described in detail in Example 2 set forth below.

Scheme 3 below illustrates a general procedure for synthesizing phenylalkyl substituted heteroaryl derivatives of formula I, inter alia, where, for example, R$^1$, R$^2$, R$^4$R$^7$, R$^8$ are hydrogen; R, R$^3$, R$^5$ and R$^6$ are chlorine; A is (CH$_2$)$_f$ where f is 1; B is O, a is 1, and D is O; b is 2; E is (E8); c and d are 0; R$^{11}$ is 4-trifluoromethylphenyl:

Scheme 3:

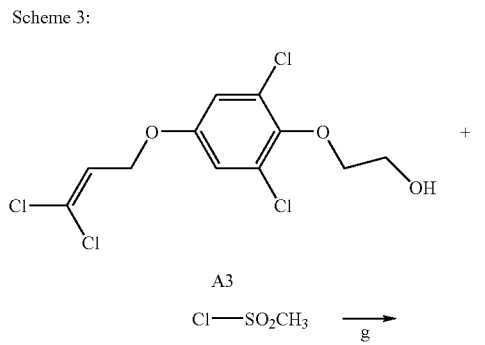

-continued

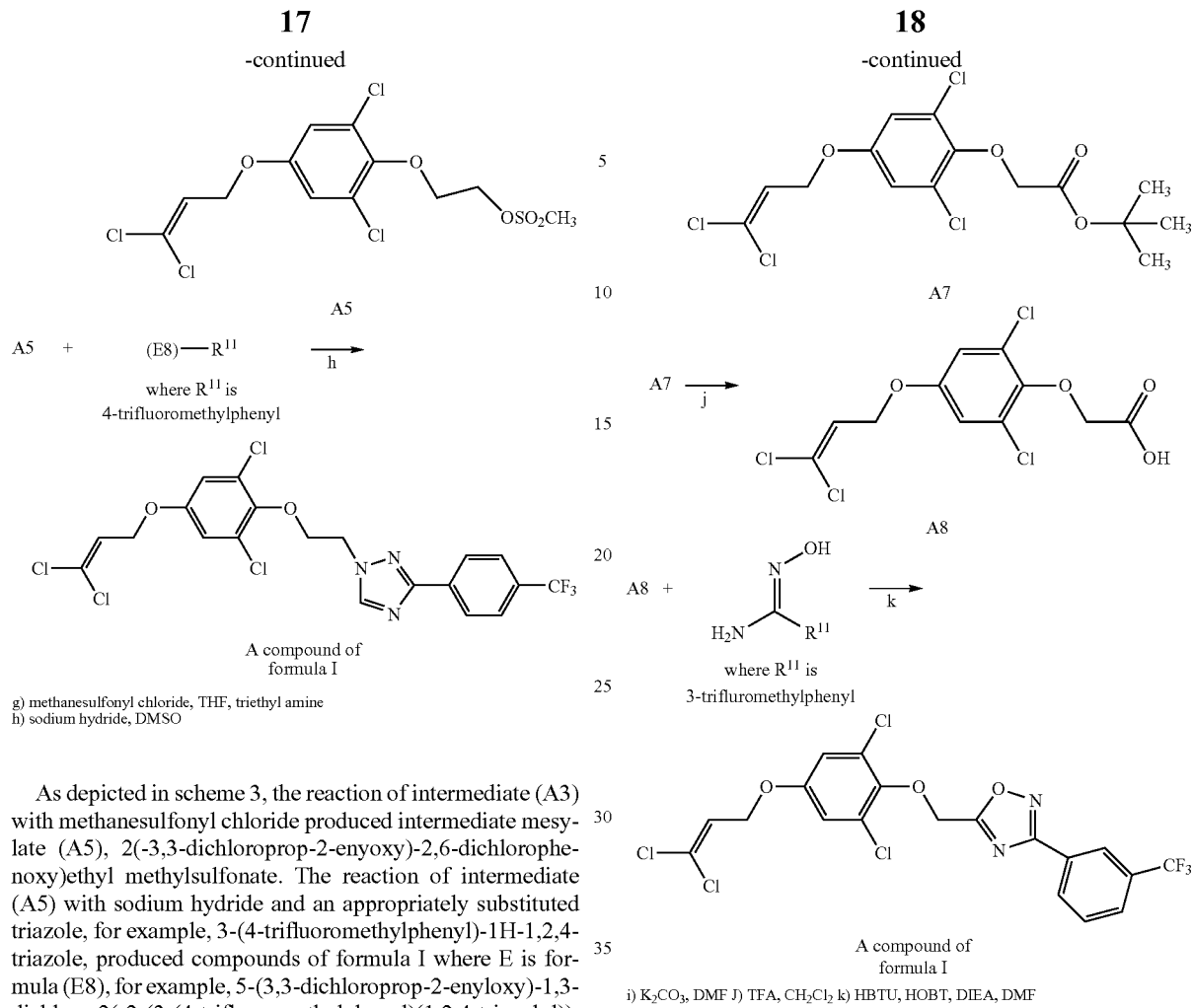

g) methanesulfonyl chloride, THF, triethyl amine
h) sodium hydride, DMSO i) K₂CO₃, DMF J) TFA, CH₂Cl₂ k) HBTU, HOBT, DIEA, DMF As depicted in scheme 3, the reaction of intermediate (A3) with methanesulfonyl chloride produced intermediate mesylate (A5), 2(-3,3-dichloroprop-2-enyoxy)-2,6-dichlorophenoxy)ethyl methylsulfonate. The reaction of intermediate (A5) with sodium hydride and an appropriately substituted triazole, for example, 3-(4-trifluoromethylphenyl)-1H-1,2,4-triazole, produced compounds of formula I where E is formula (E8), for example, 5-(3,3-dichloroprop-2-enyloxy)-1,3-dichloro-2(-2-(3-(4-trifluoromethylphenyl)(1,2,4-triazolyl)) ethoxy)benzene. This process is described in detail in Example 3 set forth below.

Scheme 4 below illustrates a general procedure for synthesizing phenylalkyl substituted heteroaryl derivatives of formula I, inter alia, where, for example, R¹, R², R⁴R⁷, R⁸ are hydrogen; R, R³, R⁵ and R⁶ are chlorine; A is (CH₂)_f where f is 1; B is O, a is 1, and D is O; b is 1; E is (E14); c and d are 0; R¹¹ is 3-trifluoromethylphenyl:

Scheme 4:

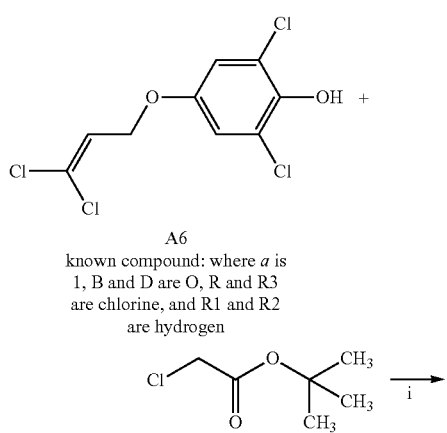

As depicted in scheme 4, the known compound 4-(3,3-dichloroprop-2-enyloxy)-2,6-dichlorophenol (A6) was reacted under basic conditions with tert-butyl chloroacetate under basic conditions, affording the corresponding tert-butyl phenoxy acetate, intermediate (A7), for example, tert-butyl 2-(4-(3,3-dichloroprop-2-enyloxy)-2,6-dichlorophenoxy) acetate. Stirring intermediate (A7) in a trifluoroacetic acid solution produced the acetic acid intermediate (A8), for example, 2-(4-(3,3-dichloroprop-2-enyloxy)-2,6-dichlorophenoxy)acetic acid. The reaction of intermediate (A8) with a benzamidoxime, for example, 3-(trifluoromethyl)benzamidoxime, in the presence of HBTU and HOBT under mild basic conditions produced the 1,2,4-oxadiazol compounds of formula I, for example, 5-(3,3-dichloroprop-2-enyloxy)-1,3-dichloro-2((3-(3-trifluoromethylphenyl)(1,2,4-oxadiazol-5-yl))methoxy)benzene. This process is described in detail in Example 4 set forth below.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or watermiscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more additional compound. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Additional compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with at least one additional compound, e.g., with other pesticides such as herbicides, the herbicides include, without limitation, for example: N-(phosphonomethyl)glycines such as glyphosate; aryloxyalkanoic acids such as 2,4-D, MCPA, and MCPP; ureas such as isoproturon; imidazolinones such as imazapyr, imazamethabenz, imazethapyr, and imazaquin; diphenyl ethers such as acifluorfen, bifenox, and fomasafen; hydroxybenzonitriles such as ioxynil and bromoxynil; sulfonylureas such as chlorimuron, achlorsulfuron, bensulfuron, pyrazosulfuron, thifensulfuron, and triasulfuron; 2-(4-aryloxyphenoxy)alkanoic acids such as fenoxaprop, fluazifop, quizalofop, and diclofop; benzothiadiazinones such as bentazone; 2-chloroacetanilides such as butachlor, metolachlor, acetochlor, and dimethenamide; arenecarboxylic acids such as dicamba; pyridyloxyacetic acids such as fluoroxypyr, aryl triazolinones such as sulfentrazone and carfentrazone-ethyl; isoxazolidinones such as clomazone; and other herbicides.

When the active insecticidal compounds of the present invention are used in combination with at least one additional compound, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alp ha-cypermethrin, beta-cypermethrin, zeta-cypermethrin, bifenthrin, cypermethrin, permethrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, imidacloprid, and other insecticides.

When the active insecticidal compounds of the present invention are used in combination with one or more of an additional compound, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with at least one additional compound, e.g., with other pesticides such as nematicides, the nematicides include, for example: carbofuran, carbosulfan, terbufos, aldecarb, ethoprop, fenamphos, oxamyl, isazofos, cadusafos, and other nematicides.

When the active insecticidal compounds of the present invention are used in combination with one or more of an additional compound, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of 5-(3,3-dichloroprop-2-enyloxy)-1,3-dichloro-2-(2-(4-(4-chlorophenyl)-1,2,3-triazolyl)ethoxy)benzene (Compound 1-2)

Step A Synthesis of 2-(2,6-dichloro-4-(phenylmethoxy)phenoxy)ethan-1-ol as an intermediate A mixture of 13 grams (0.048 mole) of 2,6-dichloro-4-phenylmethoxyphenol (known compound), 6.8 grams (0.048 mole) of potassium carbonate and 3.9 grams (0.048 mole) of 2-chloroethanol in 80 mL of DMF was heated to 70° C. where it stirred for three hours. After this time the reaction mixture was allowed to cool to ambient temperature. The reaction mixture was diluted with 100 mL of aqueous 10% hydrochloric acid then extracted with three 150 mL portions of ethyl acetate. The combined extracts were washed with an aqueous saturated sodium chloride solution, dried with magnesium sulfate and filtered. The filtrate was concentrated under reduced pressure to a residue. The crude residue was purified with column chromatography on silica gel using 6:4 heptane: ethyl acetate as an eluant. The appropriate fractions were combined and concentrated under reduced pressure, yielding 10.3 grams of the subject compound. The NMR spectrum was consistent with the proposed structure.

Step B Synthesis of 3,5-dichloro-4-(2-hydroxyethoxy)phenol as an intermediate

A mixture of 10.3 grams (0.033 mole) of 2-(2,6-dichloro-4-(phenylmethoxy)phenoxy)ethan-1-ol and 0.4 gram (catalyst) of 10% palladium on carbon in 100 mL of ethanol was subjected to hydrogenation conditions (40 PSI) using a Parr hydrogenator. After the theoretical uptake of hydrogen, the reaction mixture was filtered and concentrated under reduced pressure, yielding 7.0 grams of the subject compound as a residue. The NMR spectrum was consistent with the proposed structure.

Step C Synthesis of 2-(4-(3,3-dichloroprop-2-enyloxy)-2,6-dichlorophenoxy)ethan-1-ol as an intermediate A solution of 7.0 grams (0.386 mole) of 3,5-dichloro-4-(2-hydroxyethoxy)phenol in 60 mL of DMF was stirred, and 2.8 grams (0.039 mole) of 3-bromo-1,1,1,-trichloropropane was added, followed by 10.0 grams (0.08 mole) of potassium carbonate. Upon completion of addition the reaction mixture was heated at 95° C. during a six-hour period. After this time the reaction mixture was cooled to ambient temperature, diluted with 250 mL of water and extracted with two 150 mL portions of ethyl acetate. The extracts were combined, washed with an aqueous 10% hydrochloric acid, solution, dried with magnesium sulfate and filtered. The filtrate was concentrated under reduced pressure to a residue. The residue was purified with column chromatography on silica gel using 75:25 heptane:ethyl acetate as an eluant. The appropriate fractions were combined and concentrated under reduced pressure, yielding 4.6 grams of the subject compound. The NMR spectrum was consistent with the proposed structure.

Step D Synthesis of 4-(3,3-dichloroprop-2-enyloxy)-2,6-dichloro-1-(2-azidoethoxy)benzene as an intermediate A mixture of 1.0 gram (0.003 mole) of 2-(4-(3,3-dichloro-prop-2-enyloxy)-2,6-dichlorophenoxy)ethan-1-ol, 0.33 gram (0.0033 mole) of TEA and 0.37 gram (0.0032 mole) of methanesulfonyl chloride in 10 mL of methylene chloride was stirred at ambient temperature for two hours. The reaction mixture was diluted with 25 mL of methylene chloride and was washed first with 25 mL of water followed by 10 mL of a saturated aqueous sodium chloride solution. The organic phase was dried with magnesium sulfate, filtered and the filtrate concentrated under reduced pressure leaving an oil, which solidified upon standing. The solid was dissolved in 10 mL of DMSO to which 0.32 gram (0.005 mole) of sodium azide was added. The reaction mixture stirred at ambient temperature for about 18 hours at which time the reaction mixture was heated at 60° C. for one hour. The mixture was allowed to cool to ambient temperature, diluted with 25 mL of water and extracted with two 25 mL portions of ethyl acetate. The combined extracts were washed with 20 mL of an aqueous saturated sodium chloride solution, dried with magnesium sulfate and filtered. The filtrate was concentrated under reduced pressure providing 0.86 gram of the subject compound as a foam. The NMR spectrum was consistent with the proposed structure.

Step E Synthesis of 5-(3,3-dichloroprop-2-enyloxy)-1,3-dichloro-2-(2-(4-(4-chlorophenyl)1,2,3-triazolyl))ethoxy)benzene (Compound 2)

To a stirred mixture of 0.36 gram (0.001 mole) of 4-(3,3-dichloroprop-2-enyloxy)-2,6-dichloro-1-(2-azidoethoxy)benzene and 0.14 gram (0.0001 mole) of 1-chloro-4-ethynyl-benzene in 5 mL of a 1 to 1 mixture of t-butanol and water was added 0.1 mL of a 1M solution of sodium ascorbate in water and a catalytic amount (approximately 0.0002 gram) of copper (II) sulfate pentahydrate. The reaction mixture was allowed to stir at ambient temperature for about 18 hours, and then was diluted with 10 mL of water. The mixture was extracted with two 5 mL portions of ethyl acetate and the combined extracts were dried with magnesium sulfate and filtered. The filtrate was concentrated under reduced pressure providing 0.45 gram of the subject compound as an oil. The NMR spectrum was consistent with the proposed structure.

EXAMPLE 2

This example illustrates one protocol for the preparation of 5-(3,3-dichloroprop-2-enyloxy)-1,3-dichloro-2(-2-(5-(3-trifluoromethylphenyl)(1,2,3,4-tetraazol-2-yl))ethoxy)benzene (Compound 7-54)

Diisopropyl azodicarboxalate (0.056 gram, 0.00028 mole) was added to a stirred, cold (0° C.) mixture of 0.072 gram (0.00028 mole) of triphenylphosphine, 0.045 gram (0.00021 mole) of 5-(3-trifluoromethylphenyl)-2H-1,2,3,4-tetrazole and 0.075 gram (0.00023 mole) of 2-(4-(3,3-dichloroprop-2-enyloxy)-2,6-dichlorophenoxy)ethan-1-ol. The cold reaction mixture stirred for one hour at which time the mixture was concentrated under reduced pressure to a residue. The residue was subjected to column chromatography on silica gel, eluting with hexanes:ethyl (80:20). The appropriate fractions were combined and concentrated under reduced pressure to yield 0.125 gram of an oil. This oil was combined with similarly obtained oils from three reactions preformed in a similar manner. The combined oil was further purified by column chromatography on silica gel, eluting with mixtures of hexanes, methylene chloride and ethyl acetate to yield 0.267 gram of the subject compound as an oil. The NMR spectrum was consistent with the proposed structure.

EXAMPLE 3

This example illustrates one protocol for the preparation of 5-(3,3-dichloroprop-2-enyloxy)-1,3-dichloro-2-(2-(3-(4-trifluoromethylphenyl)(1,2,4-triazolyl))ethoxy)benzene (Compound 8-2)

Step A Synthesis of 2(-3,3-dichloroprop-2-enyloxy)-2,6-dichlorophenoxy)ethyl methylsulfonate as an intermediate To a stirred mixture of 0.25 gram (0.00075 mole) of 2-(4-(3,3-dichloroprop-2-enyloxy)-2,6-dichlorophenoxy)ethan-1-ol and 0.113 gram (0.00113 mole) of triethylamine in 3.75 mL of THF was added 0.086 gram (0.00075 mole) of methane sulfonyl chloride. The reaction mixture was stirred at ambient temperature for one hour. After this time the reaction mixture was diluted with 5 mL of aqueous ammonium chloride solution then extracted with two 7 mL portions of diethyl ether. The extracts were combined, dried with sodium sulfate and filtered. The filtrate was concentrated under reduced pressure to yield 0.31 gram of the subject compound as an oil.

Step B Synthesis of 5-(3,3-dichloroprop-2-enyloxy)-1,3-dichloro-2(-2-(3-(4-trifluoromethylphenyl)(1,2,4-triazolyl))ethoxy)benzene A mixture of 0.1 gram (0.00046 mole) of 3-(4-trifluoromethylphenyl)-1H-1,2,4-triazole and 0.01 gram (0.00042 mole) of sodium hydride (60% in mineral oil) in 2.0 mL of DMSO was stirred at ambient temperature for 15 minutes. A solution of 0.172 gram (0.00042 mole) of 2(-3,3-dichloroprop-2-enyloxy)-2,6-dichlorophenoxy)ethyl methylsulfonate dissolved in a small amount of DMSO was added to the reaction mixture. After complete addition the reaction mixture was heated to 90° C., where it stirred for about 18 hours. The reaction mixture was allowed to cool, diluted with 0.5 mL of aqueous sodium bicarbonate then extracted with 15 mL of a mixture of hexanes and ethyl acetate (7:3). The extract was washed with two 5 mL portions of water and one 5 mL portion of saturated aqueous sodium chloride solution, dried with sodium sulfate and filtered. The filtrate was concentrated under reduced pressure to an oil residue. The oil residue was purified by column chromatography on silica gel, eluted with mixtures of methylene chloride and diethyl ether. The appropriate fractions were combined and concentrated under reduced pressure, yielding 0.1 gram of the subject compound as an off-white solid.

EXAMPLE 4

This example illustrates one protocol for the preparation of 5-(3,3-dichloroprop-2-enyloxy)-1,3-dichloro-2((3-(3-trifluoromethylphenyl)(1,2,4-oxadiazol-5-yl))methoxy)benzene (Compound 14-54)

Step A Synthesis of tert-butyl 2-(4-(3,3-dichloroprop-2-enyloxy)-2,6-dichlorophenoxy)acetate as an intermediate A mixture of 0.5 gram (0.0017 mole) of 4-(3,3-dichloroprop-2-enyloxy)-2,6-dichlorophenol (known compound), 0.26 gram (0.0019 mole) of potassium carbonate and 0.26 gram (0.0017 mole) of tert-butyl chloroacetate in 0.12 mL of DMF was heated to 70° C. where it stirred for about 18 hours. After this time the reaction mixture was allowed to cool to ambient temperature. The reaction mixture was diluted with 30 mL of water then extracted with three 30 mL portions of ethyl acetate. The combined extracts were dried with sodium sulfate and filtered. The filtrate was concentrated under reduced pressure to a yellow oil. The crude oil was purified with column chromatography on silica gel using a mixture of hexanes and ethyl acetate (93:7) as an eluant. The appropriate fractions were combined and concentrated under reduced pressure, yielding 0.7 gram of the subject compound.

Step B Synthesis of 2-(4-(3,3-dichloroprop-2-enyloxy)-2,6-dichlorophenoxy)acetic acid as an intermediate A mixture of 0.3 gram (0.0008 mole) of tert-butyl 2-(4-(3,3-dichloroprop-2-enyloxy)-2,6-dichlorophenoxy)acetate in 3.0 mL of methylene chloride was stirred and cooled to 0° C. Trifluoroacetic acid (3.0 mL, 0.04 mole) was added and the reaction mixture was allowed to warm to ambient temperature where it stirred for two hours. The reaction mixture was concentrated under reduced pressure leaving a residue. The residue was dissolved in methylene chloride and the solution concentrated under reduced pressure and the resulting residue was dissolved in methylene chloride again. The solution was concentrated under reduced pressure to yield a quantitative amount of the subject compound as a white powder.

Step C Synthesis of 5-(3,3-dichloroprop-2-enyloxy)-1,3-dichloro-2((3-(3-trifluoromethylphenyl)(1,2,4-oxadiazol-5-yl))methoxy)benzene (Compound 14-54)

To a stirred solution of 0.129 gram (0.00037 mole) of 2-(4-(3,3-dichloroprop-2-enyloxy)-2,6-dichlorophenoxy)acetic acid in 1.9 mL of DMF was added 0.141 gram (0.00037 mole) of HBTU, 0.008 gram (0.00006 mole) of HOBT and 0.24 gram (0.0019 mole) of DIEA. The reaction mixture stirred for 10 minutes at which time 0.075 gram (0.00037 mole) of 3-(trifluoromethyl)benzamidoxime was added. Upon completion of addition the reaction mixture was stirred at ambient temperature then heated to 112° C. where it stirred for four hours. After this time the reaction mixture was cooled to ambient temperature, diluted with water and extracted with a mixture of hexanes and ethyl acetate (70:30). The extract was washed in succession with two 5 mL portions of water, one 5 mL portion of an aqueous hydrochloric acid solution and one 5 mL portion of aqueous sodium bicarbonate, dried with sodium sulfate and filtered. The filtrate was concentrated under reduced pressure to a residue. The residue was purified with column chromatography on silica gel using a mixture of hexanes and ethyl acetate as an eluant. The appropriate fractions were combined and concentrated under reduced pressure, yielding 0.35 gram of the subject compound as an off-white solid.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some compounds of formula I:

TABLE 1

Phenylalkyl Substituted Cyclic Urea Derivatives

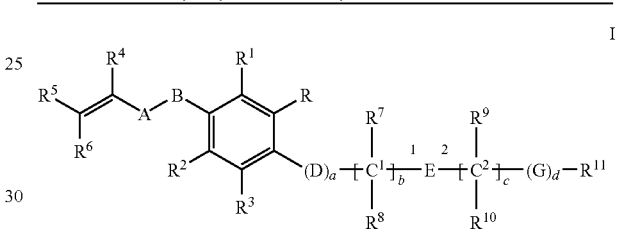

Table I-1
Formula I where $R^1$, $R^2$, $R^4$ $R^7$, $R^8$, $R^9$, $R^{10}$ are hydrogen;
R, $R^3$, $R^5$ and $R^6$ are chlorine; A is $(CH_2)_f$ where f is 1;
B is O, a is 1, and D is O; E is (E1); G is O; providing the following compounds:

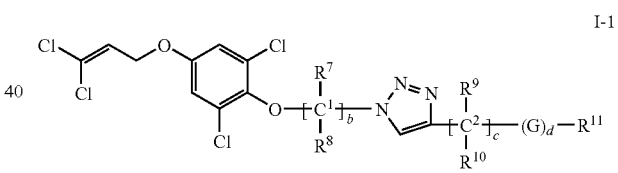

| Cmpd. No | b | c | d | $R^{11}$ |
|---|---|---|---|---|
| 1-1 | 2 | 0 | 0 | ⟨phenyl⟩-CF₃ |
| 1-2 | 2 | 0 | 0 | ⟨phenyl⟩-Cl |
| 1-3 | 2 | 0 | 0 | ⟨phenyl⟩-Cl, Cl |
| 1-4 | 2 | 1 | 0 | ⟨phenyl⟩ |
| 1-5 | 2 | 1 | 0 | ⟨cyclopentyl⟩ |

TABLE 1-continued
| | | | | |
|---|---|---|---|---|
| 1-6 | 2 | 1 | 0 | 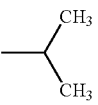 |
| 1-7 | 2 | 0 | 0 | 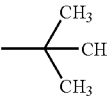 |
| 1-8 | 2 | 0 | 0 | 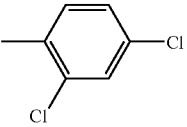 |
| 1-9 | 3 | 0 | 0 | 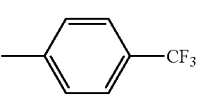 |
| 1-10 | 4 | 0 | 0 | 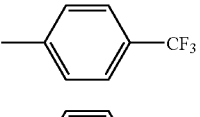 |
| 1-11 | 2 | 0 | 0 | 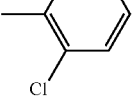 |
| 1-12 | 2 | 0 | 0 | 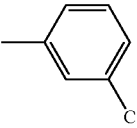 |
| 1-13 | 2 | 0 | 0 | 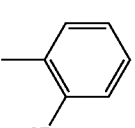 |
| 1-14 | 2 | 0 | 0 | 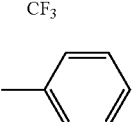 |
| 1-15 | 2 | 0 | 0 | 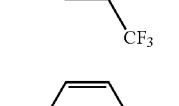 |
| 1-16 | 2 | 0 | 0 | 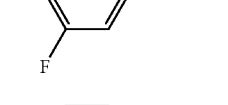 |
| 1-17 | 2 | 0 | 0 | 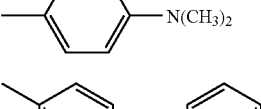 |
| 1-18 | 2 | 0 | 0 | 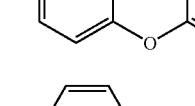 |
| 1-19 | 3 | 0 | 0 | Si(CH$_3$)$_3$ |
| 1-20 | 2 | 0 | 0 | 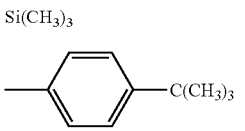 |
| 1-21 | 2 | 0 | 0 | 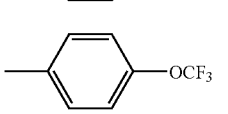 |
| 1-22 | 2 | 1 | 0 | 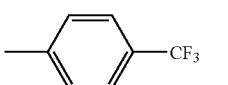 |
| 1-23 | 2 | 1 | 0 | 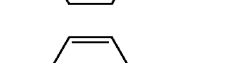 |
| 1-24 | 2 | 1 | 0 | 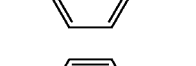 |
| 1-25 | 2 | 1 | 0 | 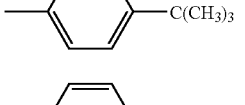 |
| 1-26 | 3 | 0 | 0 | 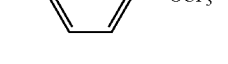 |
| 1-27 | 3 | 0 | 0 | 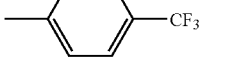 |
| 1-28 | 3 | 0 | 0 | 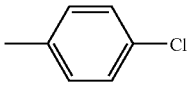 |
| 1-29 | 3 | 0 | 0 | 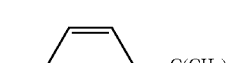 |
| 1-30 | 2 | 0 | 0 | 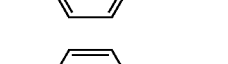 |
| 1-31 | 2 | 0 | 0 | 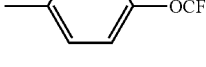 |
| 1-32 | 2 | 0 | 0 | 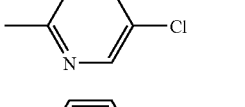 |
| 1-33 | 2 | 1 | 0 | 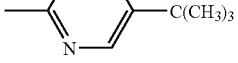 |
| 1-34 | 2 | 1 | 0 | 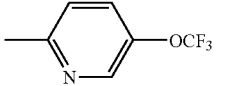 |

TABLE 1-continued
| | | | | |
|---|---|---|---|---|
| 1-35 | 2 | 1 | 0 | 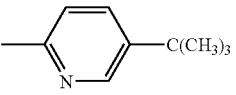 |
| 1-36 | 2 | 1 | 0 | 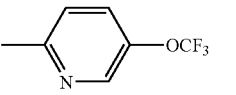 |
| 1-37 | 3 | 0 | 0 | 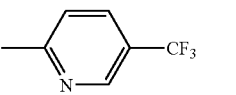 |
| 1-38 | 3 | 0 | 0 | 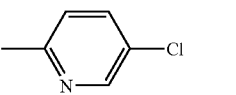 |
| 1-39 | 3 | 0 | 0 | 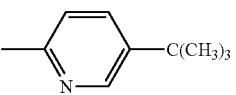 |
| 1-40 | 3 | 0 | 0 | 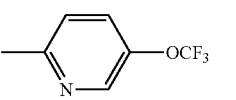 |
| 1-41 | 2 | 0 | 0 | 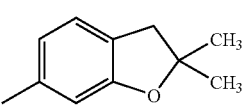 |
| 1-42 | 2 | 0 | 0 | 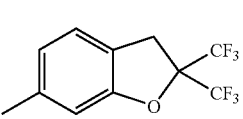 |
| 1-43 | 2 | 0 | 0 | 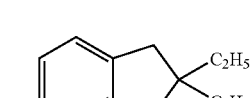 |
| 1-44 | 2 | 0 | 0 | 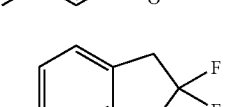 |
| 1-45 | 2 | 0 | 0 | 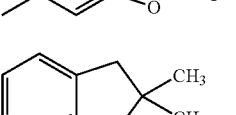 |
| 1-46 | 2 | 0 | 0 | 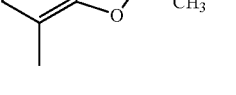 |
| 1-47 | 2 | 0 | 0 | 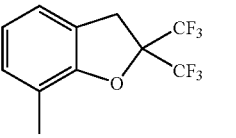 |
| 1-48 | 2 | 0 | 0 | 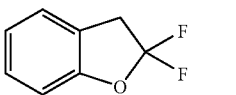 |
| 1-49 | 2 | 1 | 0 | 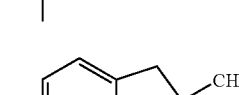 |
| 1-50 | 2 | 1 | 0 | 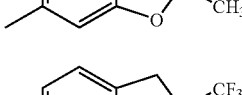 |
| 1-51 | 2 | 1 | 0 | 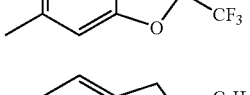 |
| 1-52 | 2 | 1 | 0 | 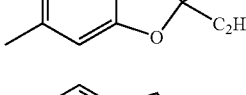 |
| 1-53 | 3 | 0 | 0 | 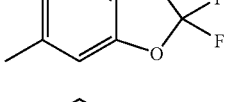 |
| 1-54 | 3 | 0 | 0 | 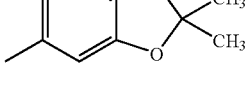 |
| 1-55 | 3 | 0 | 0 | 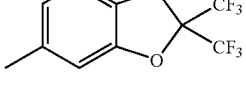 |
| 1-56 | 3 | 0 | 0 | 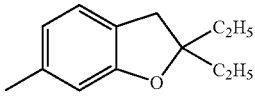 |
| 1-57 | 2 | 0 | 0 | 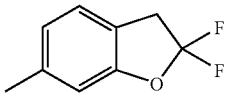 |
| 1-58 | 2 | 0 | 0 | 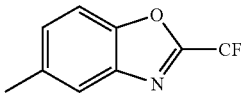 |
| 1-59 | 2 | 0 | 0 | 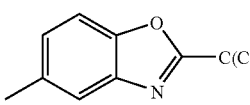 |
| 1-60 | 2 | 0 | 0 | 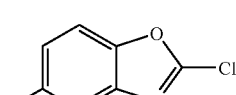 |

TABLE 1-continued
| | | | | |
|---|---|---|---|---|
| 1-61 | 2 | 0 | 0 | 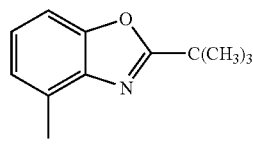 |
| 1-62 | 2 | 0 | 0 | 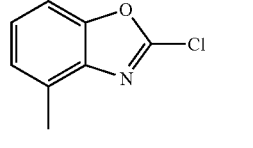 |
| 1-63 | 2 | 1 | 0 | 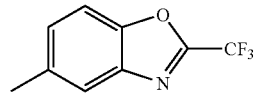 |
| 1-64 | 2 | 1 | 0 | 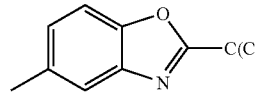 |
| 1-65 | 2 | 1 | 0 | 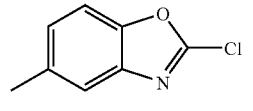 |
| 1-66 | 3 | 0 | 0 | 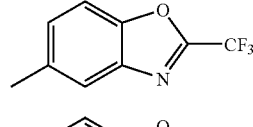 |
| 1-67 | 3 | 0 | 0 | 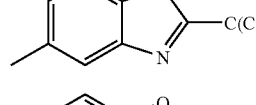 |
| 1-68 | 3 | 0 | 0 | 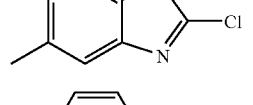 |
| 1-69 | 2 | 1 | 1 | 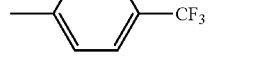 |
Table I-2
Formula I where $R^1$, $R^2$, $R^4$ $R^7$, $R^8$, $R^9$, $R^{10}$ are hydrogen; R, $R^3$, $R^5$ and $R^6$ are chlorine; A is $(CH_2)_f$ where f is 1; B is O, a is 1, and D is O; E is (E2); G is O; providing the following compounds:
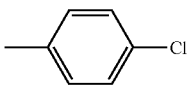   I-2
| Cmpd. No | b | c | d | $R^{11}$ |
|---|---|---|---|---|
| 2-1 | 2 | 0 | 0 | 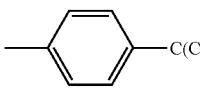 |
| 2-2 | 2 | 0 | 0 | 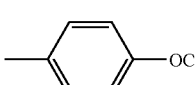 |
TABLE 1-continued
| | | | | |
|---|---|---|---|---|
| 2-3 | 2 | 0 | 0 | 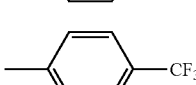 |
| 2-4 | 2 | 0 | 0 | 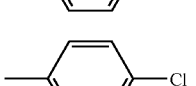 |
| 2-5 | 2 | 0 | 0 | 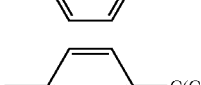 |
| 2-6 | 2 | 1 | 0 |  |
| 2-7 | 2 | 1 | 0 | 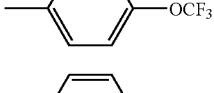 |
| 2-8 | 2 | 1 | 0 | 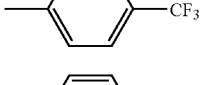 |
| 2-9 | 2 | 1 | 0 | 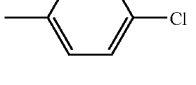 |
| 2-10 | 3 | 0 | 0 | 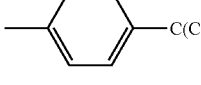 |
| 2-11 | 3 | 0 | 0 | 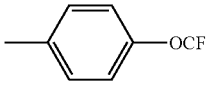 |
| 2-12 | 3 | 0 | 0 | 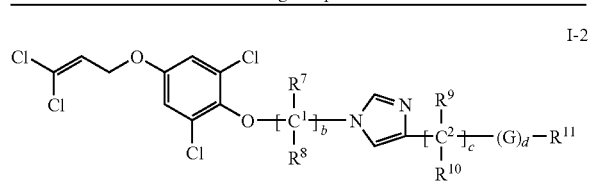 |
| 2-13 | 3 | 0 | 0 | 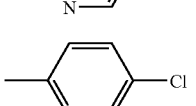 |
| 2-14 | 2 | 0 | 0 | 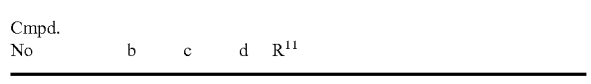 |
| 2-15 | 2 | 0 | 0 | 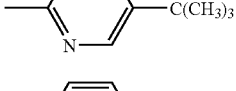 |
| 2-16 | 2 | 0 | 0 | 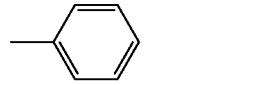 |
| 2-17 | 2 | 0 | 0 | 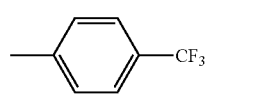 |
| 2-18 | 2 | 1 | 0 | |

TABLE 1-continued
| | | | | |
|---|---|---|---|---|
| 2-19 | 2 | 1 | 0 | 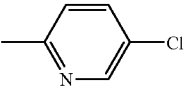 |
| 2-20 | 2 | 1 | 0 | 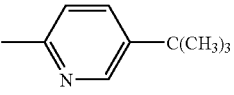 |
| 2-21 | 2 | 1 | 0 | 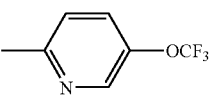 |
| 2-22 | 3 | 0 | 0 | 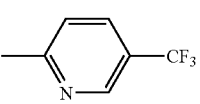 |
| 2-23 | 3 | 0 | 0 | 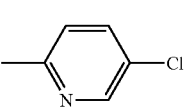 |
| 2-24 | 3 | 0 | 0 | 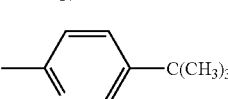 |
| 2-25 | 3 | 0 | 0 | 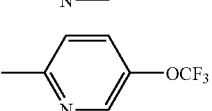 |
| 2-26 | 2 | 0 | 0 | 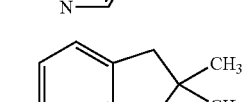 |
| 2-27 | 2 | 0 | 0 | 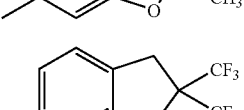 |
| 2-28 | 2 | 0 | 0 | 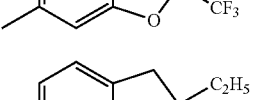 |
| 2-29 | 2 | 0 | 0 | 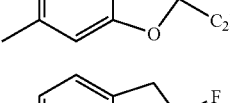 |
| 2-30 | 2 | 0 | 0 | 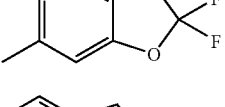 |
| 2-31 | 2 | 0 | 0 | 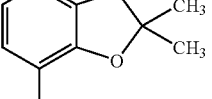 |
| 2-32 | 2 | 0 | 0 | 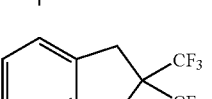 |
TABLE 1-continued
| | | | | |
|---|---|---|---|---|
| 2-33 | 2 | 0 | 0 | 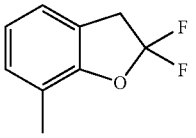 |
| 2-34 | 2 | 1 | 0 | 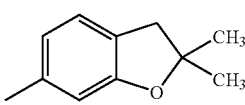 |
| 2-35 | 2 | 1 | 0 | 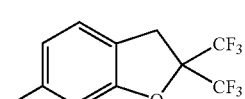 |
| 2-36 | 2 | 1 | 0 | 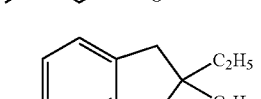 |
| 2-37 | 2 | 1 | 0 | 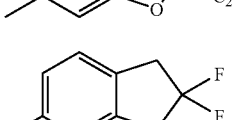 |
| 2-38 | 3 | 0 | 0 | 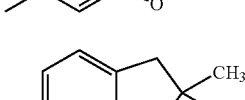 |
| 2-39 | 3 | 0 | 0 | 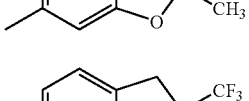 |
| 2-40 | 3 | 0 | 0 | 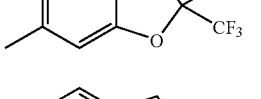 |
| 2-41 | 3 | 0 | 0 | 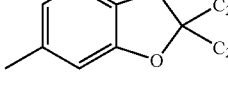 |
| 2-42 | 2 | 0 | 0 | 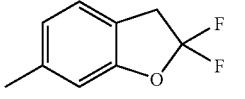 |
| 2-43 | 2 | 0 | 0 | 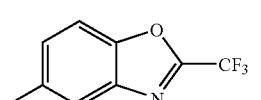 |
| 2-44 | 2 | 0 | 0 | 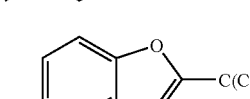 |
| 2-45 | 2 | 0 | 0 | 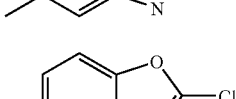 |

TABLE 1-continued

| Cmpd. No | b | c | d | R¹¹ |
|---|---|---|---|---|
| 2-46 | 2 | 0 | 0 | 4-methyl-benzoxazol-2-yl-C(CH₃)₃ |
| 2-47 | 2 | 0 | 0 | 4-methyl-benzoxazol-2-yl-Cl |
| 2-48 | 2 | 1 | 0 | 5-methyl-benzoxazol-2-yl-CF₃ |
| 2-49 | 2 | 1 | 0 | 5-methyl-benzoxazol-2-yl-C(CH₃)₃ |
| 2-50 | 2 | 1 | 0 | 5-methyl-benzoxazol-2-yl-Cl |
| 2-51 | 3 | 0 | 0 | 5-methyl-benzoxazol-2-yl-CF₃ |
| 2-52 | 3 | 0 | 0 | 5-methyl-benzoxazol-2-yl-C(CH₃)₃ |
| 2-53 | 3 | 0 | 0 | 5-methyl-benzoxazol-2-yl-Cl |

Table I-3, All the compounds set forth in Table I-2 wherein E is (E3)

Table I-4
Formula I where R¹, R², R⁴ R⁷, R⁸, R⁹, R¹⁰ are hydrogen;
R, R³, R⁵ and R⁶ are chlorine; A is (CH₂)_f where f is 1;
B is O, a is 1, and D is O; E is (E4); G is O; providing the
following compounds:

I-4

Structure: Cl₂C=CH-CH₂-O-(2,6-dichlorophenyl)-O-[C¹(R⁷)(R⁸)]_b-(1,2,3-triazol-4-yl, N-substituted)-[C²(R⁹)(R¹⁰)]_c-(G)_d-R¹¹

| Cmpd. No | b | c | d | R¹¹ |
|---|---|---|---|---|
| 4-1 | 2 | 0 | 0 | phenyl |
| 4-2 | 2 | 0 | 0 | 4-CF₃-phenyl |
| 4-3 | 2 | 0 | 0 | 4-Cl-phenyl |
| 4-4 | 2 | 0 | 0 | 4-C(CH₃)₃-phenyl |
| 4-5 | 2 | 0 | 0 | 4-OCF₃-phenyl |
| 4-6 | 2 | 1 | 0 | 4-CF₃-phenyl |
| 4-7 | 2 | 1 | 0 | 4-Cl-phenyl |
| 4-8 | 2 | 1 | 0 | 4-C(CH₃)₃-phenyl |
| 4-9 | 2 | 1 | 0 | 4-OCF₃-phenyl |
| 4-10 | 3 | 0 | 0 | 4-CF₃-phenyl |
| 4-11 | 3 | 0 | 0 | 4-Cl-phenyl |
| 4-12 | 3 | 0 | 0 | 4-C(CH₃)₃-phenyl |
| 4-13 | 3 | 0 | 0 | 4-OCF₃-phenyl |
| 4-14 | 2 | 0 | 0 | 5-CF₃-pyridin-2-yl |
| 4-15 | 2 | 0 | 0 | 5-Cl-pyridin-2-yl |
| 4-16 | 2 | 0 | 0 | 5-C(CH₃)₃-pyridin-2-yl |
| 4-17 | 2 | 0 | 0 | 5-OCF₃-pyridin-2-yl |
| 4-18 | 2 | 1 | 0 | 5-CF₃-pyridin-2-yl |

TABLE 1-continued
| | | | | |
|---|---|---|---|---|
| 4-19 | 2 | 1 | 0 | 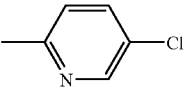 |
| 4-20 | 2 | 1 | 0 | 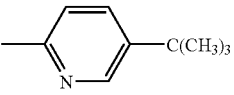 |
| 4-21 | 2 | 1 | 0 | 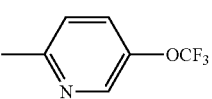 |
| 4-22 | 3 | 0 | 0 | 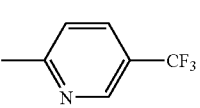 |
| 4-23 | 3 | 0 | 0 | 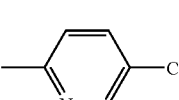 |
| 4-24 | 3 | 0 | 0 | 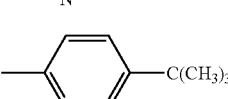 |
| 4-25 | 3 | 0 | 0 | 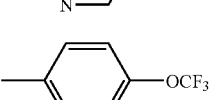 |
| 4-26 | 2 | 0 | 0 | 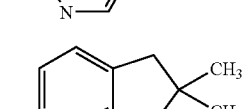 |
| 4-27 | 2 | 0 | 0 | 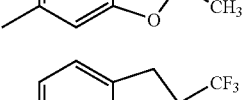 |
| 4-28 | 2 | 0 | 0 | 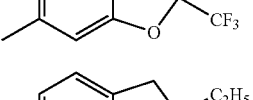 |
| 4-29 | 2 | 0 | 0 | 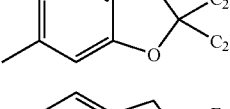 |
| 4-30 | 2 | 0 | 0 | 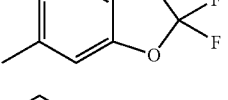 |
| 4-31 | 2 | 0 | 0 | 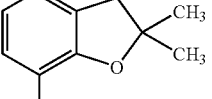 |
| 4-32 | 2 | 0 | 0 | 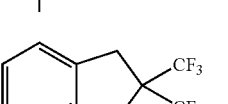 |
| 4-33 | 2 | 0 | 0 | 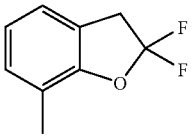 |
| 4-34 | 2 | 1 | 0 | 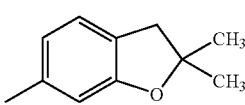 |
| 4-35 | 2 | 1 | 0 | 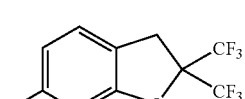 |
| 4-36 | 2 | 1 | 0 | 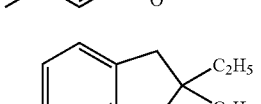 |
| 4-37 | 2 | 1 | 0 | 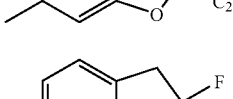 |
| 4-38 | 3 | 0 | 0 | 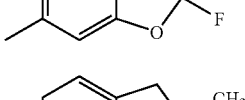 |
| 4-39 | 3 | 0 | 0 | 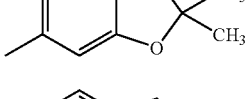 |
| 4-40 | 3 | 0 | 0 | 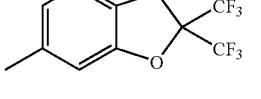 |
| 4-41 | 3 | 0 | 0 | 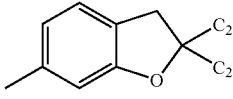 |
| 4-42 | 2 | 0 | 0 | 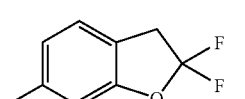 |
| 4-43 | 2 | 0 | 0 | 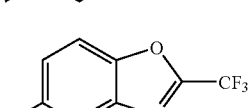 |
| 4-44 | 2 | 0 | 0 | 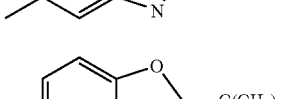 |
| 4-45 | 2 | 0 | 0 | 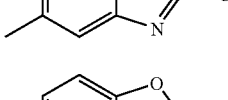 |

TABLE 1-continued
| 4-46 | 2 | 0 | 0 | 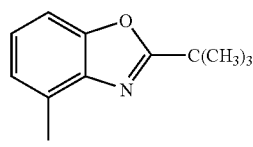 |
| --- | --- | --- | --- | --- |
| 4-47 | 2 | 0 | 0 | 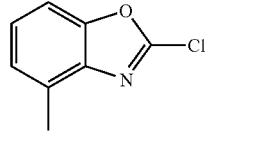 |
| 4-48 | 2 | 1 | 0 | 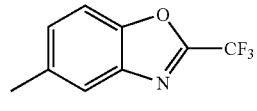 |
| 4-49 | 2 | 1 | 0 | 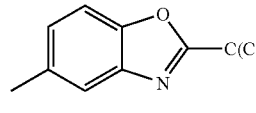 |
| 4-50 | 2 | 1 | 0 | 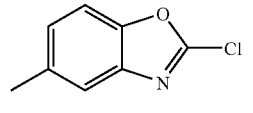 |
| 4-51 | 3 | 0 | 0 | 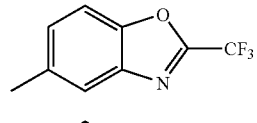 |
| 4-52 | 3 | 0 | 0 | 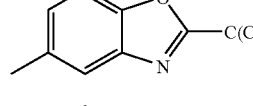 |
| 4-53 | 3 | 0 | 0 | 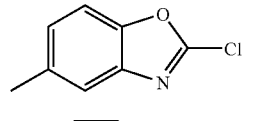 |
| 4-54 | 1 | 0 | 0 | 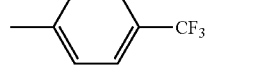 |
Table I-5, All the compounds set forth in Table I-2 wherein E is (E5)
Table I-6, All the compounds set forth in Table I-2 wherein E is (E6)
Table I-7
Formula I where $R^1$, $R^2$, $R^4$ $R^7$, $R^8$, $R^9$, $R^{10}$ are hydrogen; R, $R^3$, $R^5$ and $R^6$ are chlorine; A is $(CH_2)_f$ where f is 1; B is O, a is 1, and D is O; E is (E7); G is O; providing the following compounds:
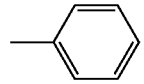
I-7
| Cmpd. No | b | c | d | $R^{11}$ |
| --- | --- | --- | --- | --- |
| 7-1 | 2 | 0 | 0 | 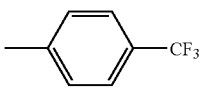 |
| 7-2 | 2 | 0 | 0 | 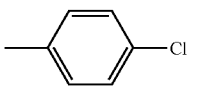 |
| 7-3 | 2 | 0 | 0 | 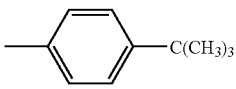 |
| 7-4 | 2 | 0 | 0 | 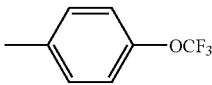 |
| 7-5 | 2 | 0 | 0 | 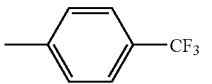 |
| 7-6 | 2 | 1 | 0 | 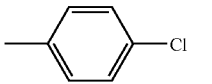 |
| 7-7 | 2 | 1 | 0 | 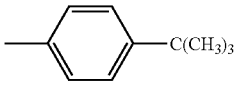 |
| 7-8 | 2 | 1 | 0 | 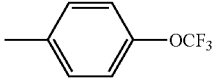 |
| 7-9 | 2 | 1 | 0 | 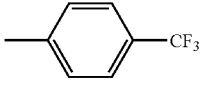 |
| 7-10 | 3 | 0 | 0 | 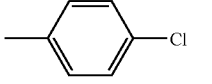 |
| 7-11 | 3 | 0 | 0 | 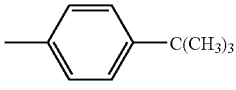 |
| 7-12 | 3 | 0 | 0 | 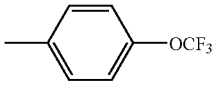 |
| 7-13 | 3 | 0 | 0 | 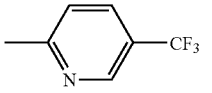 |
| 7-14 | 2 | 0 | 0 | 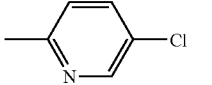 |
| 7-15 | 2 | 0 | 0 | |
| 7-16 | 2 | 0 | 0 | |
| 7-17 | 2 | 0 | 0 | |

TABLE 1-continued
| | | | | |
|---|---|---|---|---|
| 7-18 | 2 | 1 | 0 | 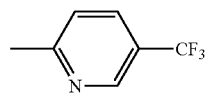 |
| 7-19 | 2 | 1 | 0 | 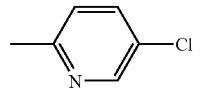 |
| 7-20 | 2 | 1 | 0 | 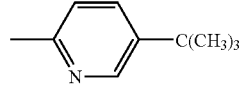 |
| 7-21 | 2 | 1 | 0 | 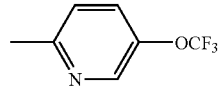 |
| 7-22 | 3 | 0 | 0 | 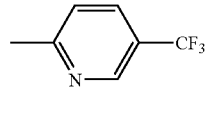 |
| 7-23 | 3 | 0 | 0 | 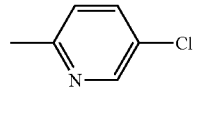 |
| 7-24 | 3 | 0 | 0 | 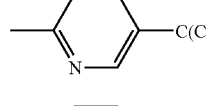 |
| 7-25 | 3 | 0 | 0 | 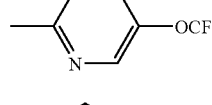 |
| 7-26 | 2 | 0 | 0 | 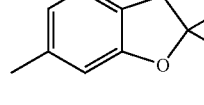 |
| 7-27 | 2 | 0 | 0 | 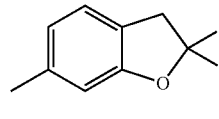 |
| 7-28 | 2 | 0 | 0 | 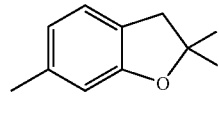 |
| 7-29 | 2 | 0 | 0 | 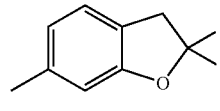 |
| 7-30 | 2 | 0 | 0 | 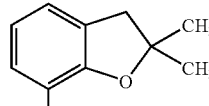 |
| 7-31 | 2 | 0 | 0 | 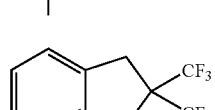 |
| 7-32 | 2 | 0 | 0 | 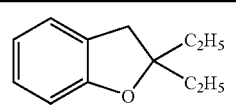 |
| 7-33 | 2 | 0 | 0 | 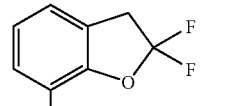 |
| 7-34 | 2 | 1 | 0 | 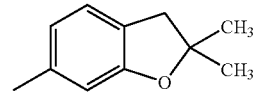 |
| 7-35 | 2 | 1 | 0 | 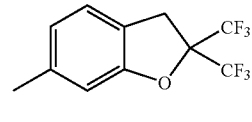 |
| 7-36 | 2 | 1 | 0 | 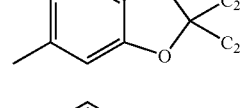 |
| 7-37 | 2 | 1 | 0 | 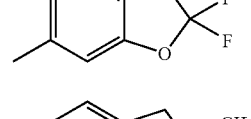 |
| 7-38 | 3 | 0 | 0 | 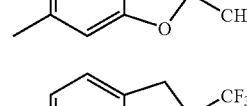 |
| 7-39 | 3 | 0 | 0 | 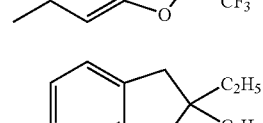 |
| 7-40 | 3 | 0 | 0 | 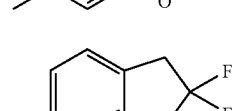 |
| 7-41 | 3 | 0 | 0 | 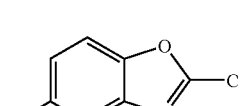 |
| 7-42 | 2 | 0 | 0 | 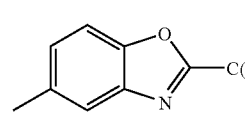 |
| 7-43 | 2 | 0 | 0 | 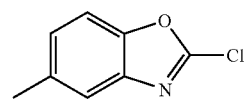 |
| 7-44 | 2 | 0 | 0 |  |

TABLE 1-continued

| 7-45 | 2 | 0 | 0 | 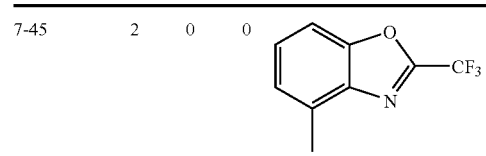 |
| --- | --- | --- | --- | --- |
| 7-46 | 2 | 0 | 0 | 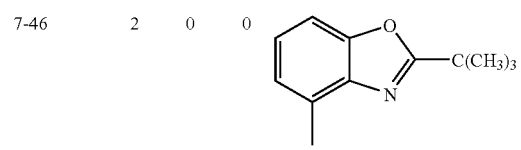 |
| 7-47 | 2 | 0 | 0 | 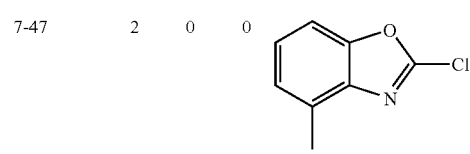 |
| 7-48 | 2 | 1 | 0 | 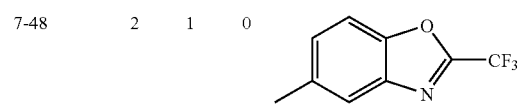 |
| 7-49 | 2 | 1 | 0 | 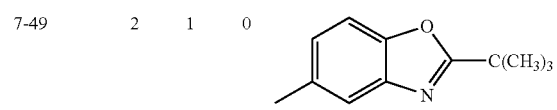 |
| 7-50 | 2 | 1 | 0 | 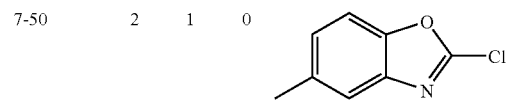 |
| 7-51 | 3 | 0 | 0 | 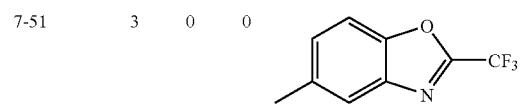 |
| 7-52 | 3 | 0 | 0 | 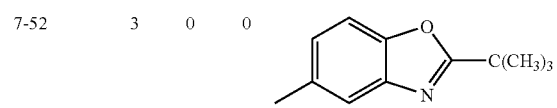 |
| 7-53 | 3 | 0 | 0 | 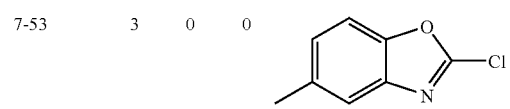 |
| 7-54 | 2 | 0 | 0 | 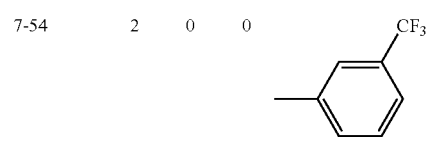 |
| 7-55 | 2 | 0 | 0 | 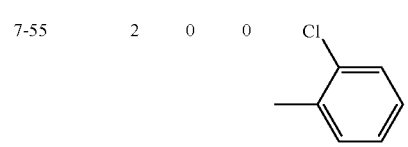 |
| 7-56 | 2 | 0 | 0 | 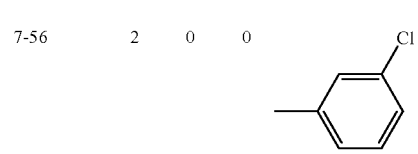 |

TABLE 1-continued

Table I-8
Formula I where $R^1$, $R^2$, $R^4$ $R^7$, $R^8$, $R^9$, $R^{10}$ are hydrogen; R, $R^3$, $R^5$ and $R^6$ are chlorine; A is $(CH_2)_f$ where f is 1; B is O, a is 1, and D is O; E is (E8); G is O; providing the following compounds:

I-8

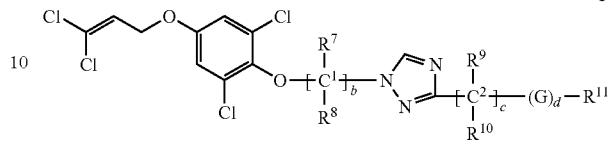

| Cmpd. No | b | c | d | $R^{11}$ |
| --- | --- | --- | --- | --- |
| 8-1 | 2 | 0 | 0 | —⟨C₆H₅⟩ |
| 8-2 | 2 | 0 | 0 | —⟨C₆H₄⟩—CF₃ |
| 8-3 | 2 | 0 | 0 | —⟨C₆H₄⟩—Cl |
| 8-4 | 2 | 0 | 0 | —⟨C₆H₄⟩—C(CH₃)₃ |
| 8-5 | 2 | 0 | 0 | —⟨C₆H₄⟩—OCF₃ |
| 8-6 | 2 | 1 | 0 | —⟨C₆H₄⟩—CF₃ |
| 8-7 | 2 | 1 | 0 | —⟨C₆H₄⟩—Cl |
| 8-8 | 2 | 1 | 0 | —⟨C₆H₄⟩—C(CH₃)₃ |
| 8-9 | 2 | 1 | 0 | —⟨C₆H₄⟩—OCF₃ |
| 8-10 | 3 | 0 | 0 | —⟨C₆H₄⟩—CF₃ |
| 8-11 | 3 | 0 | 0 | —⟨C₆H₄⟩—Cl |
| 8-12 | 3 | 0 | 0 | —⟨C₆H₄⟩—C(CH₃)₃ |
| 8-13 | 3 | 0 | 0 | —⟨C₆H₄⟩—OCF₃ |

TABLE 1-continued
| | | | | |
|---|---|---|---|---|
| 8-14 | 2 | 0 | 0 | 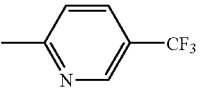 |
| 8-15 | 2 | 0 | 0 | 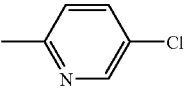 |
| 8-16 | 2 | 0 | 0 | 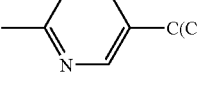 |
| 8-17 | 2 | 0 | 0 | 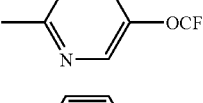 |
| 8-18 | 2 | 1 | 0 | 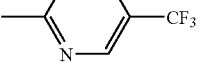 |
| 8-19 | 2 | 1 | 0 | 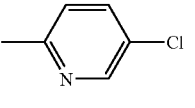 |
| 8-20 | 2 | 1 | 0 | 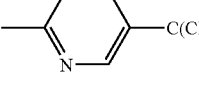 |
| 8-21 | 2 | 1 | 0 | 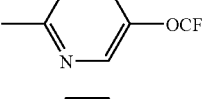 |
| 8-22 | 3 | 0 | 0 | 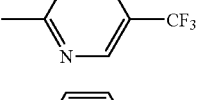 |
| 8-23 | 3 | 0 | 0 | 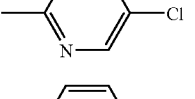 |
| 8-24 | 3 | 0 | 0 | 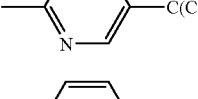 |
| 8-25 | 3 | 0 | 0 | 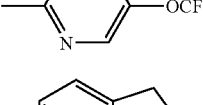 |
| 8-26 | 2 | 0 | 0 | 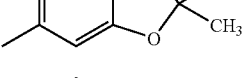 |
| 8-27 | 2 | 0 | 0 | 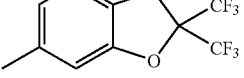 |
| 8-28 | 2 | 0 | 0 | 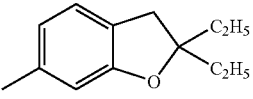 |
| 8-29 | 2 | 0 | 0 | 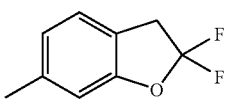 |
| 8-30 | 2 | 0 | 0 | 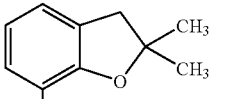 |
| 8-31 | 2 | 0 | 0 | 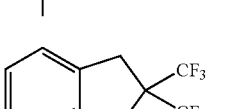 |
| 8-32 | 2 | 0 | 0 | 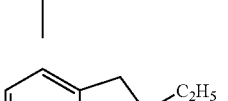 |
| 8-33 | 2 | 0 | 0 | 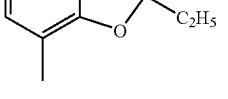 |
| 8-34 | 2 | 1 | 0 | 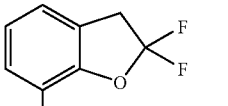 |
| 8-35 | 2 | 1 | 0 | 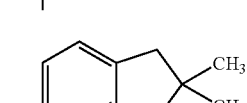 |
| 8-36 | 2 | 1 | 0 | 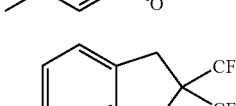 |
| 8-37 | 2 | 1 | 0 | 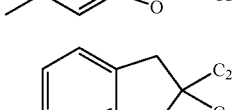 |
| 8-38 | 3 | 0 | 0 | 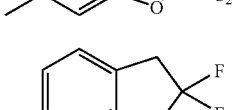 |
| 8-39 | 3 | 0 | 0 | 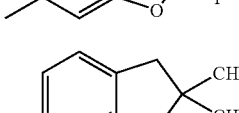 |
| 8-40 | 3 | 0 | 0 | 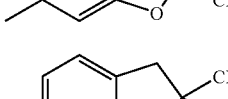 |
| 8-41 | 3 | 0 | 0 | 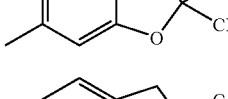 |

TABLE 1-continued

| 8-42 | 2 | 0 | 0 | 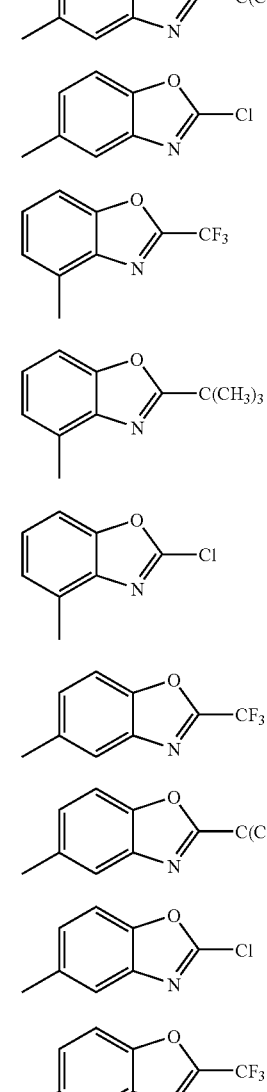 |
| --- | --- | --- | --- | --- |
| 8-43 | 2 | 0 | 0 | 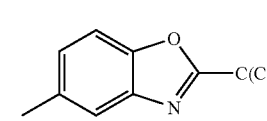 |
| 8-44 | 2 | 0 | 0 | 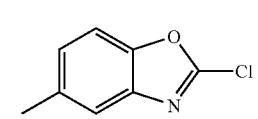 |
| 8-45 | 2 | 0 | 0 | 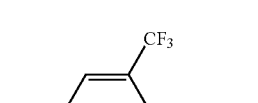 |
| 8-46 | 2 | 0 | 0 | 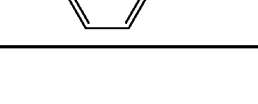 |
| 8-47 | 2 | 0 | 0 |  |
| 8-48 | 2 | 1 | 0 | 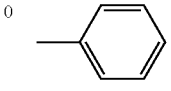 |
| 8-49 | 2 | 1 | 0 | 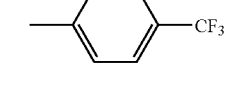 |
| 8-50 | 2 | 1 | 0 | 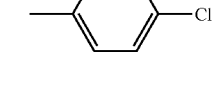 |
| 8-51 | 3 | 0 | 0 | 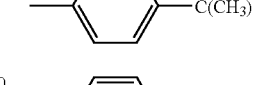 |
| 8-52 | 3 | 0 | 0 | 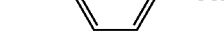 |
| 8-53 | 3 | 0 | 0 | 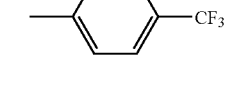 |
| 8-54 | 1 | 0 | 0 | 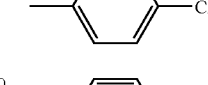 |

TABLE 1-continued

Table I-9, All the compounds set forth in Table I-2 wherein E is (E9)

Table I-10, All the compounds set forth in Table I-2 wherein E is (E10)

Table I-11, All the compounds set forth in Table I-2 wherein E is (E11)

Table I-12, All the compounds set forth in Table I-2 wherein E is (E12)

Table I-13, All the compounds set forth in Table I-2 wherein E is (E13)

Table I-14
Formula I where $R^1$, $R^2$, $R^4$ $R^7$, $R^8$, $R^9$, $R^{10}$ are hydrogen; R, $R^3$, $R^5$ and $R^6$ are chlorine; A is $(CH_2)_f$ where f is 1; B is O, a is 1, and D is O; E is (E14); G is O; providing the following compounds:

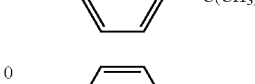

I-14

| Cmpd. No | b | c | d | $R^{11}$ |
| --- | --- | --- | --- | --- |
| 14-1 | 2 | 0 | 0 | 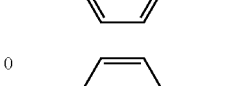 |
| 14-2 | 2 | 0 | 0 | 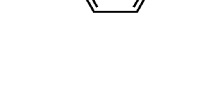 |
| 14-3 | 2 | 0 | 0 | —⟨⟩—Cl |
| 14-4 | 2 | 0 | 0 | —⟨⟩—C(CH₃)₃ |
| 14-5 | 2 | 0 | 0 | —⟨⟩—OCF₃ |
| 14-6 | 2 | 1 | 0 | —⟨⟩—CF₃ |
| 14-7 | 2 | 1 | 0 | —⟨⟩—Cl |
| 14-8 | 2 | 1 | 0 | —⟨⟩—C(CH₃)₃ |
| 14-9 | 2 | 1 | 0 | —⟨⟩—OCF₃ |
| 14-10 | 3 | 0 | 0 | —⟨⟩—CF₃ |

TABLE 1-continued

| | | | | |
|---|---|---|---|---|
| 14-11 | 3 | 0 | 0 | 4-Cl-phenyl |
| 14-12 | 3 | 0 | 0 | 4-C(CH$_3$)$_3$-phenyl |
| 14-13 | 3 | 0 | 0 | 4-OCF$_3$-phenyl |
| 14-14 | 2 | 0 | 0 | 5-CF$_3$-pyridin-2-yl |
| 14-15 | 2 | 0 | 0 | 5-Cl-pyridin-2-yl |
| 14-16 | 2 | 0 | 0 | 5-C(CH$_3$)$_3$-pyridin-2-yl |
| 14-17 | 2 | 0 | 0 | 5-OCF$_3$-pyridin-2-yl |
| 14-18 | 2 | 1 | 0 | 5-CF$_3$-pyridin-2-yl |
| 14-19 | 2 | 1 | 0 | 5-Cl-pyridin-2-yl |
| 14-20 | 2 | 1 | 0 | 5-C(CH$_3$)$_3$-pyridin-2-yl |
| 14-21 | 2 | 1 | 0 | 5-OCF$_3$-pyridin-2-yl |
| 14-22 | 3 | 0 | 0 | 5-CF$_3$-pyridin-2-yl |
| 14-23 | 3 | 0 | 0 | 5-Cl-pyridin-2-yl |
| 14-24 | 3 | 0 | 0 | 5-C(CH$_3$)$_3$-pyridin-2-yl |
| 14-25 | 3 | 0 | 0 | 5-OCF$_3$-pyridin-2-yl |
| 14-26 | 2 | 0 | 0 | 2,2-diCH$_3$-6-methyl-2,3-dihydrobenzofuran |
| 14-27 | 2 | 0 | 0 | 2,2-diCF$_3$-6-methyl-2,3-dihydrobenzofuran |
| 14-28 | 2 | 0 | 0 | 2,2-diC$_2$H$_5$-6-methyl-2,3-dihydrobenzofuran |
| 14-29 | 2 | 0 | 0 | 2,2-diF-6-methyl-2,3-dihydrobenzofuran |
| 14-30 | 2 | 0 | 0 | 2,2-diCH$_3$-7-methyl-2,3-dihydrobenzofuran |
| 14-31 | 2 | 0 | 0 | 2,2-diCF$_3$-7-methyl-2,3-dihydrobenzofuran |
| 14-32 | 2 | 0 | 0 | 2,2-diC$_2$H$_5$-7-methyl-2,3-dihydrobenzofuran |
| 14-33 | 2 | 0 | 0 | 2,2-diF-7-methyl-2,3-dihydrobenzofuran |
| 14-34 | 2 | 1 | 0 | 2,2-diCH$_3$-6-methyl-2,3-dihydrobenzofuran |
| 14-35 | 2 | 1 | 0 | 2,2-diCF$_3$-6-methyl-2,3-dihydrobenzofuran |
| 14-36 | 2 | 1 | 0 | 2,2-diC$_2$H$_5$-6-methyl-2,3-dihydrobenzofuran |
| 14-37 | 2 | 1 | 0 | 2,2-diF-6-methyl-2,3-dihydrobenzofuran |
| 14-38 | 3 | 0 | 0 | 2,2-diCH$_3$-6-methyl-2,3-dihydrobenzofuran |

TABLE 1-continued

| | | | | |
|---|---|---|---|---|
| 14-39 | 3 | 0 | 0 | 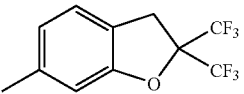 |
| 14-40 | 3 | 0 | 0 | 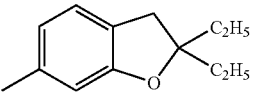 |
| 14-41 | 3 | 0 | 0 | 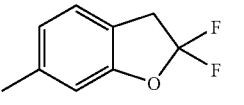 |
| 14-42 | 2 | 0 | 0 | 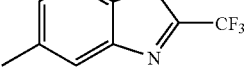 |
| 14-43 | 2 | 0 | 0 | 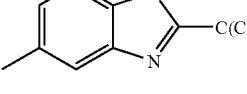 |
| 14-44 | 2 | 0 | 0 | 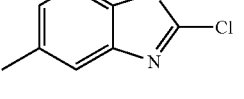 |
| 14-45 | 2 | 0 | 0 | 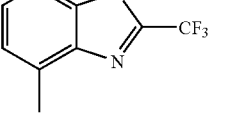 |
| 14-46 | 2 | 0 | 0 | 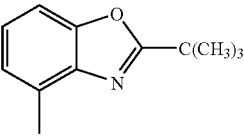 |
| 14-47 | 2 | 0 | 0 | 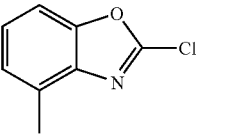 |
| 14-48 | 2 | 1 | 0 | 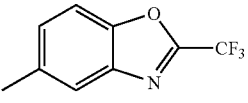 |
| 14-49 | 2 | 1 | 0 | 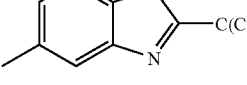 |
| 14-50 | 2 | 1 | 0 | 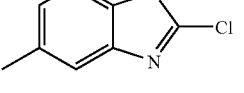 |
| 14-51 | 3 | 0 | 0 | 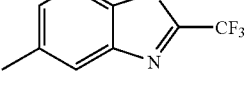 |
| 14-52 | 3 | 0 | 0 | 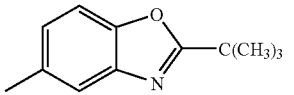 |
| 14-53 | 3 | 0 | 0 | 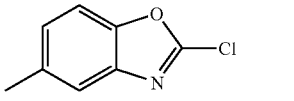 |
| 14-54 | 1 | 0 | 0 | 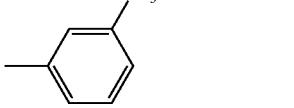 |

| |
|---|
| Table I-15, All the compounds set forth in Table I-2 wherein E is (E15) |
| Table I-16, All the compounds set forth in Table I-2 wherein E is (E16) |
| Table I-17, All the compounds set forth in Table I-2 wherein E is (E17) |
| Table I-18, All the compounds set forth in Table I-2 wherein E is (E18) |
| Table I-19, All the compounds set forth in Table I-2 wherein E is (E19) |
| Table I-20, All the compounds set forth in Table I-2 wherein E is (E20) |
| Table I-21, All the compounds set forth in Table I-2 wherein E is (E21) |
| Table I-22, All the compounds set forth in Table I-2 wherein E is (E22) wherein bond 1 is at position '2' and bond 2 is at position '5' |
| Table I-23, All the compounds set forth in Table I-2 wherein E is (E23) wherein bond 1 is at position '2' and bond 2 is at position '5' |
| Table I-24, All the compounds set forth in Table I-2 wherein E is (E24) |
| Table I-25, All the compounds set forth in Table I-2 wherein E is (E25) |
| Table I-26, All the compounds set forth in Table I-2 wherein E is (E26) |
| Table I-27, All the compounds set forth in Table I-2 wherein E is (E27) |
| Table I-28, All the compounds set forth in Table I-2 wherein E is (E28) |
| Table I-29, All the compounds set forth in Table I-2 wherein E is (E29) |
| Table I-30, All the compounds set forth in Table I-2 wherein E is (E30) |
| Table I-31, All the compounds set forth in Table I-2 wherein E is (E31) |
| Table I-32, All the compounds set forth in Table I-2 wherein E is (E32) |
| Table I-33, All the compounds set forth in Table I-2 wherein E is (E33) |
| Table I-34, All the compounds set forth in Table I-2 wherein E is (E34) |
| Table I-35, All the compounds set forth in Table I-2 wherein E is (E35) |

The following table sets forth physical characterizing data for certain compounds of formula I of the present invention. The test compounds of formula I are identified by numbers that correspond to those in Table 1:

The following table sets forth physical characterizing data for certain compounds of formula I of the present invention. The test compounds of formula I are identified by numbers that correspond to those in Table 1:

TABLE 2

Phenylalkyl Substituted Cyclic Urea Derivatives Compound Characterization

| | Molecular Formula | Melting Point (° C.) of Solids Or Physical State |
|---|---|---|
| 1-1 | $C_{20}H_{14}Cl_4F_3N_3O_2$ | 99-101 |
| 1-2 | $C_{19}H_{14}Cl_5N_3O_2$ | FOAM |
| 1-3 | $C_{19}H_{13}Cl_6N_3O_2$ | OIL |
| 1-4 | $C_{20}H_{17}Cl_4N_3O_2$ | OIL |
| 1-5 | $C_{19}H_{21}Cl_4N_3O_2$ | OIL |
| 1-6 | $C_{17}H_{19}Cl_4N_3O_2$ | OIL |
| 1-7 | $C_{17}H_{19}Cl_4N_3O_2$ | OIL |
| 1-8 | $C_{19}H_{13}Cl_6N_3O_2$ | 116-118 |
| 1-9 | $C_{21}H_{16}Cl_4F_3N_3O_2$ | 87-88 |
| 1-10 | $C_{22}H_{18}Cl_4F_3N_3O_2$ | 112-113 |
| 1-11 | $C_{19}H_{14}Cl_5N_3O_2$ | 120-121 |
| 1-12 | $C_{19}H_{14}Cl_5N_3O_2$ | 73-75 |
| 1-13 | $C_{20}H_{14}Cl_4F_3N_3O_2$ | OIL |
| 1-14 | $C_{20}H_{14}Cl_4F_3N_3O_2$ | OIL |
| 1-15 | $C_{19}H_{13}Cl_4F_2N_3O_2$ | 112-113 |
| 1-16 | $C_{21}H_{20}Cl_4N_4O_2$ | 85-88 |
| 1-17 | $C_{25}H_{19}Cl_4N_3O_3$ | 94-95 |
| 1-18 | $C_{19}H_{13}Cl_4F_3N_4O_2$ | 115-116 |
| 1-19 | $C_{17}H_{21}Cl_4N_3O_2Si$ | OIL |
| 1-69 | $C_{21}H_{16}Cl_4F_3N_3O_3$ | 108-110 |
| 2-1 | $C_{20}H_{16}Cl_4N_2O_2$ | ORANGE OIL |
| 4-6 | $C_{21}H_{16}Cl_4F_3N_3O_2$ | OIL |
| 4-54 | $C_{19}H_{12}Cl_4F_3N_3O_2$ | 118-119 |
| 7-1 | $C_{18}H_{14}Cl_4N_4O_2$ | YELLOW OIL |
| 7-2 | $C_{19}H_{13}Cl_4F_3N_4O_2$ | COLORLESS OIL |
| 7-3 | $C_{18}H_{13}Cl_5F_3N_4O_2$ | OFF-WHITE SOLID |
| 7-54 | $C_{19}H_{13}Cl_4F_3N_4O_2$ | LIGHT YELLOW OIL |
| 7-55 | $C_{18}H_{13}Cl_5N_4O_2$ | YELLOW OIL |
| 7-56 | $C_{18}H_{13}Cl_5N_4O_2$ | YELLOW OIL |
| 8-2 | $C_{20}H_{14}Cl_4F_3N_3O_2$ | OFF-WHITE SOLID |
| 8-54 | $C_{20}H_{14}Cl_4F_3N_3O_2$ | OFF-WHITE SOLID |
| 14-2 | $C_{19}H_{11}Cl_4F_3N_3O_3$ | WHITE SOLID |
| 14-54 | $C_{19}H_{11}Cl_4F_3N_3O_3$ | OFF-WHITE SOLID |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm diameter×17.6 mm deep; Corning Costar Corp., One Alewife Center, Cambridge, Mass. 02140). The diet was allowed to cool to ambient temperature before treatment with the candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of the candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed a second instar tobacco budworm larvae, weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Certain Phenylalkyl Substituted Cyclic Urea Derivatives When Applied to the Surface of the Diet of Tobacco Budworm (*Heliothis virescens* [Fabricius])

| Cmpd. No. | Percent Mortality | Percent Growth Inhibition | Cmpd. No. | Percent Mortality | Percent Growth Inhibition |
|---|---|---|---|---|---|
| 1-1 | 100 | 100 | 1-2 | 100 | 100 |
| 1-3 | 100 | 100 | 1-4 | 100 | 100 |
| 1-5 | 100 | 100 | 1-6 | 0 | 49 |
| 1-7 | 100 | 100 | 1-8 | 0 | 33 |
| 1-9 | 100 | 100 | 1-10 | 100 | 100 |
| 1-11 | 100 | 100 | 1-12 | 100 | 100 |
| 1-13 | 100 | 100 | 1-14 | 100 | 100 |
| 1-15 | 100 | 100 | 1-16 | 67 | 91 |
| 1-17 | 67 | 100 | 1-18 | 100 | 100 |
| 1-19 | 100 | 100 | 1-69 | 17 | 71 |
| 2-1 | 100 | 100 | 4-6 | 0 | 7 |
| 4-54 | 0 | 14 | 7-1 | 100 | 100 |
| 7-2 | 100 | 100 | 7-3 | 100 | 100 |
| 7-54 | 100 | 100 | 7-55 | 100 | 100 |
| 7-56 | 100 | 100 | 8-2 | 100 | 100 |
| 8-54 | 100 | 100 | 14-2 | 100 | 100 |
| 14-54 | 100 | 100 | | | |

Concentration of the candidate insecticide on the surface of the diet is 0.25 millimolar As set forth in Table 3, most of the tested compounds of the present invention provided 100% mortality and 100% growth inhibition of the tobacco budworm.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I where
R and R³ are independently selected from hydrogen and halogen;
R¹ and R² are independently selected from hydrogen, halogen and (C₁-C₃)alkyl;
A is $(CH_2)_f$ where f is 1;
B is O;
R⁴ is hydrogen;
R⁵ and R⁶ are independently selected from halogen;
a is 1;
and when a is 1,
D is O;
b is 2;
R⁷ and R⁸ are hydrogen;
E is selected from (E1), (E2), (E3), (E4), (E5), (E6), (E7), (E8), (E9), (E16), (E17), (E24), (E25), (E26), (E27), (E28), (E29), (E30), (E33), (E34)

where 1 and 2 indicate the bond of attachment in formula I,
c is 0;
d is 0; and,
G is O;

$R^{11}$ is

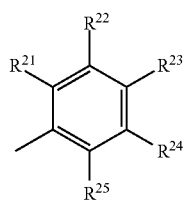

(R11-1)

wherein $R^{21}$ through $R^{25}$ are independently selected from hydrogen, halogen, $(C_1-C_6)$alkyl, $(C_2-C_4)$alkenyl, $(C_2-C_4)$alkynyl, halo$(C_1-C_6)$alkyl, hydroxy$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy$(C_1-C_6)$alkyl, $(C_2-C_4)$alkenyloxy, $(C_2-C_4)$alkynyloxy, halo$(C_1-C_6)$alkoxy, halo$(C_2-C_4)$alkenyloxy, halo$(C_2-C_4)$alkynyloxy, $(C_1-C_6)$alkylthio, $(C_1-C_6)$alkylsulfinyl, $(C_1-C_6)$alkylsulfonyl, halo$(C_1-C_6)$alkylthio, halo$(C_1-C_6)$alkylsulfinyl, halo$(C_1-C_6)$alkylsulfonyl, cyano, nitro; $NR^cR^d$, where $R^c$ and $R^d$ are independently selected from hydrogen, $(C_1-C_6)$alkyl, halo$(C_1-C_6)$alkyl, $(C_1-C_6)$alkoxy, $(C_1-C_6)$alkylcarbonyl, and $(C_1-C_6)$alkoxycarbonyl, or $R^c$ and $R^d$ are taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$alkylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy;

or an agriculturally-acceptable salt thereof.

2. A compound of claim 1, wherein
R and $R^3$ are halogen;
$R^1$, $R^2$ and $R^4$ are hydrogen;
$R^5$ and $R^6$ are halogen;
A is $(CH_2)_f$ where f is 1;
B is O;
a is 1; D is O;
b is 2; $R^7$ and $R^8$ are each hydrogen;
E is formula (E1), formula (E2), formula (E4), formula (E7) or formula (E8);
c is 0; $R^9$ and $R^{10}$ are each hydrogen;
d is 0; and
$R^{11}$ is formula ($R^{11}$–1).

3. A compound of claim 2, wherein
R and $R^3$ are each chlorine;
a is 1 and D is O;
b is 2;
E is formula (E1) or formula (E7);
c is 0;
d is 0; and
$R^{11}$ is ($R^{11}$–1).

4. A composition comprising an insecticidally effective amount of a compound of claim 1 and at least one agriculturally acceptable extender or adjuvant.

5. The insecticidal composition of claim 4, further comprising one or more additional compounds selected from the group consisting of pesticides, plant growth regulators, fertilizers and soil conditioners.

6. A method of controlling insects, comprising applying an insecticidally effective amount of a composition of claim 4 to a locus where insects are present or are expected to be present.

7. A method of controlling insects, comprising applying an insecticidally effective amount of a composition of claim 5 to a locus where insects are present or are expected to be present.

* * * * *